US007127279B2

(12) United States Patent
Finneran et al.

(10) Patent No.: US 7,127,279 B2
(45) Date of Patent: Oct. 24, 2006

(54) EMG ELECTRODE APPARATUS AND POSITIONING SYSTEM

(75) Inventors: Mark T. Finneran, Wooster, OH (US); Kathryn E. Alexander, Colombus, OH (US); B. Russell Alexander, Colombus, OH (US); Charles E. Wickham, Jr., Glenford, OH (US); Richard L. Hitchcock, Grove City, OH (US); Scott D. Howard, Galloway, OH (US)

(73) Assignee: SpineMatrix, Inc., Cleveland, OH (US)

( * ) Notice: Subject to any disclaimer, the term of this patent is extended or adjusted under 35 U.S.C. 154(b) by 0 days.

(21) Appl. No.: 11/231,025

(22) Filed: Sep. 20, 2005

(65) Prior Publication Data

US 2006/0015028 A1   Jan. 19, 2006

Related U.S. Application Data

(62) Division of application No. 10/641,709, filed on Aug. 15, 2003, now Pat. No. 6,973,344, which is a division of application No. 09/806,632, filed as application No. PCT/US99/23033 on Oct. 4, 1999, now Pat. No. 6,745,062.

(60) Provisional application No. 60/103,105, filed on Oct. 5, 1998.

(51) Int. Cl.
  *A61B 5/0492*   (2006.01)
(52) U.S. Cl. ................. 600/393; 600/391; 600/392; 600/546

(58) Field of Classification Search ................. 600/393
See application file for complete search history.

(56) References Cited

U.S. PATENT DOCUMENTS

| 3,387,608 | A |   | 6/1968  | Figar          |         |
|-----------|---|---|---------|----------------|---------|
| 3,612,061 | A |   | 10/1971 | Collins et al. |         |
| 4,082,086 | A | * | 4/1978  | Page et al.    | 600/393 |
| 4,583,549 | A |   | 4/1986  | Manoli         |         |
| 4,763,660 | A |   | 8/1988  | Kroll et al.   |         |
| 4,957,109 | A |   | 9/1990  | Groeger et al. |         |

(Continued)

*Primary Examiner*—Lee S. Cohen
(74) *Attorney, Agent, or Firm*—Christopher L. Parmelee; Walker & Jocke LPA

(57) ABSTRACT

A system for detecting and analyzing electrical activity in the anatomy of an organism underlying an electrode array provides signals corresponding to electrical activity adjacent each electrode. Such signals are correlated to the underlying anatomy of the organism and representative outputs presented through various types of output devices. Such outputs may include variations in coloration or other qualities in correspondence with representations of underlying anatomical structures. The system includes novel electrode structures (200, 224, and 284) and methods for producing and attaching electrode arrays (240 and 280) to the organism. The exemplary form of the invention is used in connection with the diagnosis of muscle activity in the lower lumbar regions of humans. Levels of muscle activity detected are analyzed by correlation with the muscular structures underlying the electrode array. Forms of the invention may be used in other applications.

9 Claims, 35 Drawing Sheets

U.S. PATENT DOCUMENTS

| | | |
|---|---|---|
| 5,163,440 A | 11/1992 | DeLuca et al. |
| 5,224,479 A | 7/1993 | Sekine |
| 5,327,888 A | 7/1994 | Imran |
| 5,341,806 A | 8/1994 | Gadsby et al. |
| 5,462,065 A | 10/1995 | Cusimano |
| 5,483,970 A | 1/1996 | Rosenberg |
| 5,660,177 A | 8/1997 | Faupel et al. |
| 5,733,151 A | 3/1998 | Edsall et al. |
| 5,772,591 A | 6/1998 | Cram |
| 6,047,202 A | 4/2000 | Finneran et al. |
| 6,052,608 A | 4/2000 | Young et al. |
| 6,055,448 A | 4/2000 | Anderson et al. |

\* cited by examiner

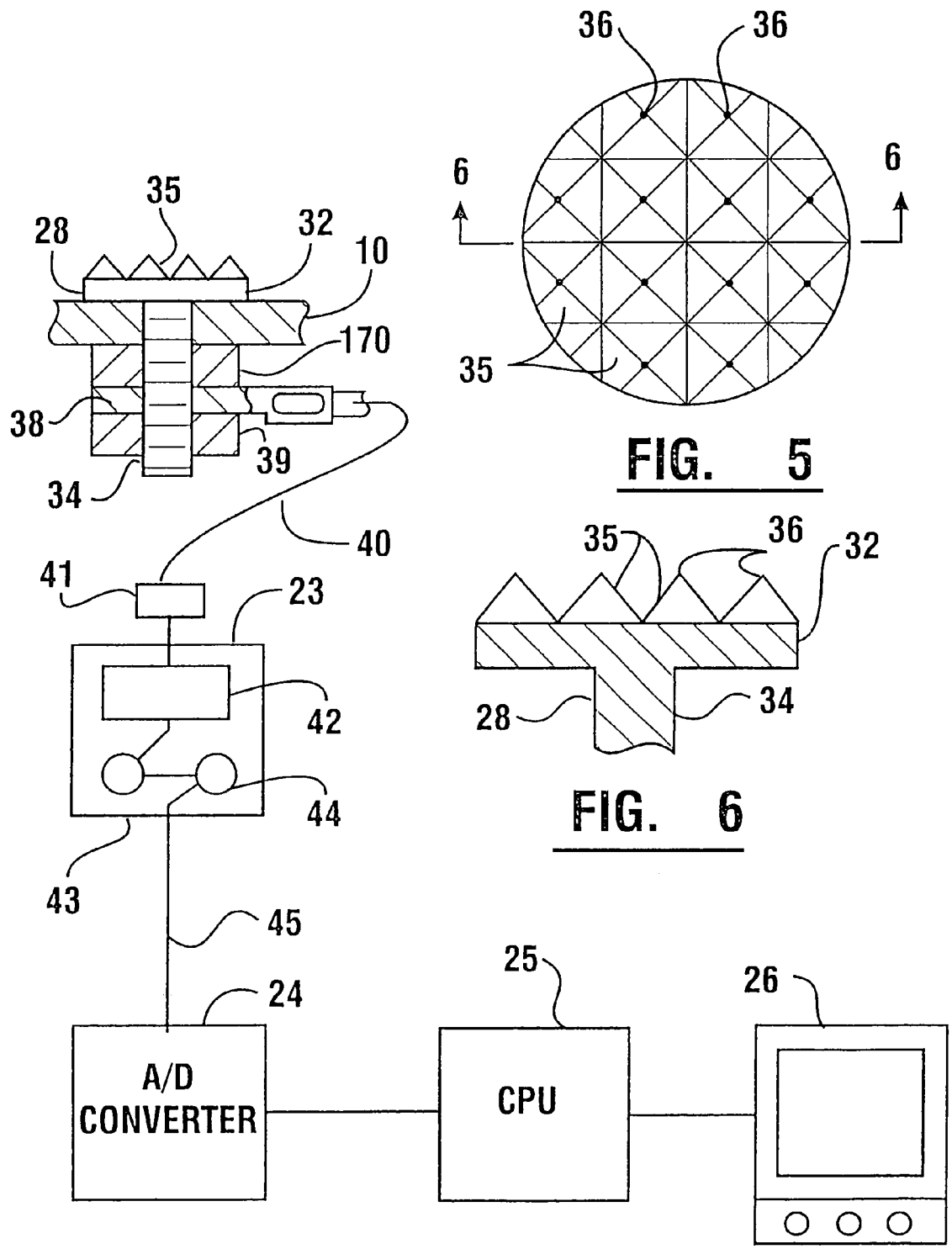
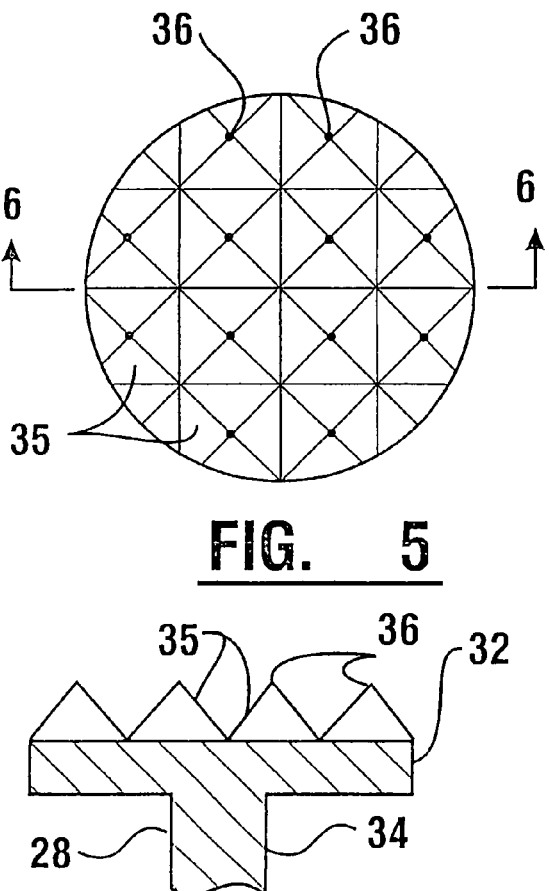
FIG. 5
FIG. 6
FIG. 4

Software Program - Header Format (135)

Version Information: (152)

File version major
File version minor

Patient Information: (154)

Patient name
Patient initials
Age
Weight
Sex
Height (Feet and Inches)
Birth date
Current date
Comments

Pad Information: (155)

Model name
Vertical number of electrodes
Horizontal number of electrodes
Vertical electrode spacing (cm)
Horizontal electrode spacing (cm)

Calibration Information: (156)

Spinous process T-10x coordinate (pixels)
Spinous process T-10y coordinate (pixels)
Left PSIS x coordinate (pixels)
Left PSIS y coordinate (pixels)
Right PSIS x coordinate (pixels)
Right PSIS y coordinate (pixels)

Data Acquisition Settings: (157)

Number of channels scanned
Pre-amplifier gain
Analog digital board gain
Scan rate (seconds)
Scan period (seconds)
Pre-scan period (milliseconds)

Display Settings: (158)

Minimum voltage to display (display software will show voltages below this value as saturated)
Maximum voltage to display (display software will show voltages above this value as saturated)

FIG. 28

Software Program - File List

Analog-to-Digital (*A2D) Files (130)

A2D files contain the actual analog-to-digital values collected from the National Instruments hardware during a test. The files contain the header described above and the Analog-to-digital values. The structure of an A/D scan is:

<Scan 1, channel 1><Scan 1, channel 1, channel 3>...
<Scan 2, channel 1><Scan 2, channel 2, channel 3>...
Etc...

Each scan is stored in a two byte word in little endian format.

Voltage (*.DAT) Files (132)

DAT files contain the voltage data from a test, after it has been converted from A/D values to voltages and signal conditioning filters have been applied. The files contain the header described above followed by the voltage values. The Format is:

<Scan 1, channel 1><Scan 1, channel 2><Scan 1, channel 3>...
<Scan 2, channel 1><Scan 2, channel 2><Scan 2, channel 3>...
etc...

Each scan is stored as an IEEE double floating point value.

RMS (*.RMS) Files (134)

RMS files contain the RMS values of the differences between the voltage waveforms of adjacent electrodes. During display of an RMS file, the values can then be mapped to colors, and displayed as colored line segments. The files contain the header described above by the RMS information.

The RMS voltage differences is calculated for each pair of adjacent electrodes. The row and column position of each of the two electrodes are also stored.

First electrodes' row number
First electrodes' column number
Second electrodes' row number
Second electrodes' column number
RMS values The following information about the RMS values is also stored:

Minimum RMS value in scan
Maximum RMS value in scan
Total number of adjacent electrodes pairs

FIG. 29

Software Program Source File Structure (160)

Document/view and visual interface: (161)

| | |
|---|---|
| PDIMFC.CPP | Main initialization of application, display of splash screen and about dialog box. |
| MAINFORM.CPP | Message handlers for main window, menu and toolbar commands |
| CHILDFORM.CPP | Message handlers for child windows (the views). |
| PDNIFCDOC.CPP | Document: handles the commands to create new RMS files open existing ones. |
| GRAPH.CPP | Document: reads RMS files and calculates the colors to display for RMS values. |
| PDINFCVIEW.CPP | View: Displays and handles user interface controls for the RMS graph display. |

Dialog popups: (162)

| | |
|---|---|
| DIALOGPATIENT. CPP | Dialog for entering patient information. |
| DIALOGCALIBRATE. CCP | Dialog for entering calibration information. |
| DIALOGDATAAQ.CPP | Dialog that allows user to launch acquisitions of data and view acquisition parameters (Scan rate, pre-amplifier gain, etc) |
| DIALOG SETTINGS. CPP | Dialog that allows editing of data acquisition and display parameters. |
| SPLASHDIALOG. CPP | Popup display of software titles and spiffy back picture. |

Data acquisition, filtering, and calculation: (163)

| | |
|---|---|
| DAQHW.CPP | Interface to National Instruments software. Sets A/D board parameters and starts data acquisition |
| READATOD.CPP | Routines for calculating RMS values, converting A/D values to voltage, and signal conditioning |
| FILTER.CPP | Filtering algorithms including high pass, low pass, and band pass with over-sampling |

Reading and writing header information and data: (164)

| | |
|---|---|
| PATIENT.CPP | Read/Write patient information. |
| CALIBRATE.CPP | Read/Write calibrate information. |
| SETTING.CPP | Read/Write settings information. |
| PAD.CPP | Read/Write pad information. |
| DATA.CPP | Read/Write A/D scan. |

Utilities: (165)

| | |
|---|---|
| FILELIST.CPP | Routines for gathering unique descriptive file names and data files. |
| SORT.CPP | Routine for preforming heap sort. |
| COMPARE. CPP | Routine passed to sort function that handles comparison. |
| STDAFX.CPP | Includes and other preprocessor definitions. |

Bitmaps, icons, resource files: (166)

| | | |
|---|---|---|
| LEVEL1A.BMP, | LEVEL5B.BMP, | |
| LEVEL1B.BMP, | LEVEL6.BMP, | |
| LEVEL2.BMP, | LEVEL7.BMP | |
| LEVEL3.BMP, | LEVEL8.BMP | Pictures of backs for use in RMS display. |
| LEVEL4.BMP, | | |
| LEVEL5A,BMP, | BITMAP1.BMP | Pad displayed in calibration dialog. |
| | SPLASH1A.BMP | Splash screen. |
| | TOOLBAR.BMP | Toolbar used at top of main window. |

FIG. 30

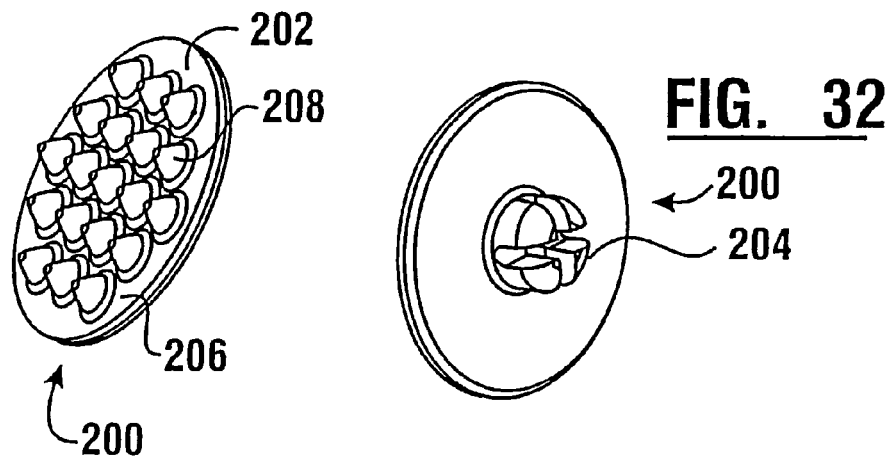
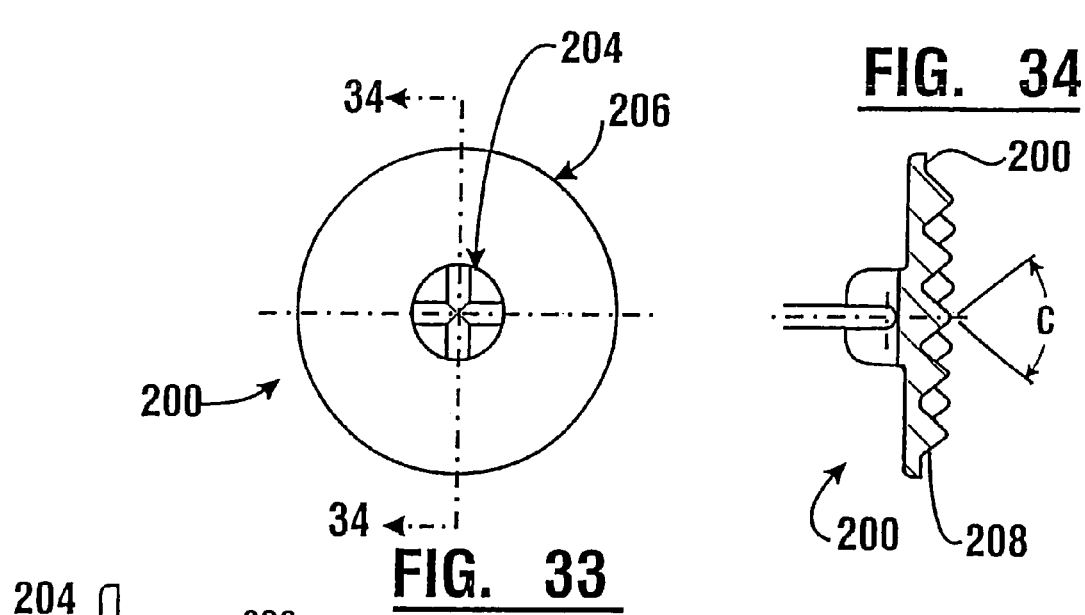
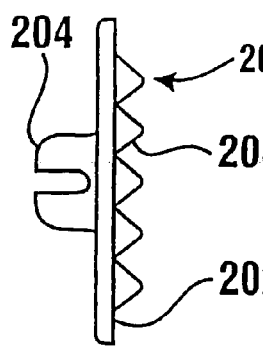
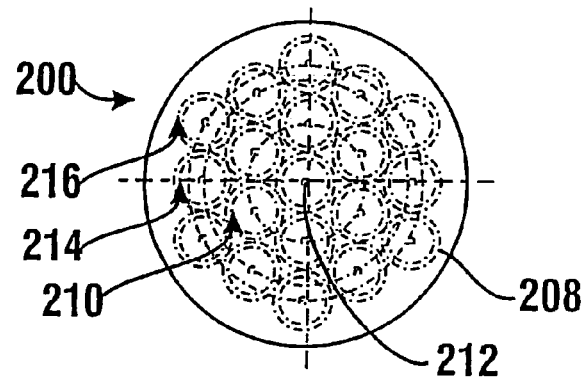

EMG ELECTRODE APPARATUS AND POSITIONING SYSTEM

This application is a divisional of application Ser. No. 10/641,709 filed Aug. 15, 2003, now U.S. Pat. No. 6,973,344, which is a divisional of application Ser. No. 09/806,632 filed on Apr. 2, 2001, now U.S. Pat. No. 6,745,062, which is a national phase application of PCT/US99/23033 filed Oct. 4, 1999 which claims the benefit of U.S. Provisional Application Ser. No. 60/103,105 filed Oct. 5, 1998.

TECHNICAL FIELD

This invention relates to a method and apparatus for monitoring and displaying the condition of muscles in a muscle group by the sensing and analysis of electromyographic signals derived from a non-invasive body surface electrode array positioned close to the muscle group. Particularly this invention relates to an electrode apparatus and a system for positioning and holding electrodes in a desired orientation relative to the anatomy of a patient.

BACKGROUND ART

Knowledge of the presence of electromyographic (EMG) signals in the muscles of humans, and the change of these signals with muscle activity, spawned development of electronic devices and techniques for monitoring those signals for the evaluation of the muscles. Human musculature, however, involves many hundreds of muscles in various muscle groups, which interact to provide skeletal support and movement. Much of the recent development has been concerned with the techniques and/or devices for monitoring the signals, analyzing the information obtained and providing reliable and useful data for the patient or treating physician. Recent developments in computer technology have also provided an assist in this regard. With higher speeds of operation and greater computing capacity, the capability for handling and operating upon a multiplicity of signals in a reasonable evaluation period has become feasible. However, because of the complexity of the muscle structure and the difficulty in obtaining useful, reliable signals, preferably in a non-invasive mode, obtaining a useful definition of the muscle activity in a reasonable amount of time and in an economical manner is still subject to current development.

Typical of this prior art is the device described by D. Prutchi in the publication "A High-Resolution Large Array (HRLA) EMG System", published September 1995 in Med. Eng. Phys., Vol. 17, 442–454. Prutchi describes a bracelet which may be wrapped about a body limb and which contains 256 surface electrodes to record the electrical activity of underlying muscles. The electrodes are arranged in eight groups of thirty-two electrode linear arrays directly connected to buffer boards in close proximity of the electrodes. Further processing of the electrical signals is performed to provide a desired signal analysis, in this instance primarily being concerned with the bidirectional propagation of a compound potential in a single muscle in the upper arm of a human subject or a histogram of total power contribution from active fibers in a subject muscle, both being presented in charted format.

U.S. Pat. No. 5,086,779 to DeLuca, et al., describes a back analysis system of plural electrodes coupled to a computer system for processing the signals and to provide graphical representations of results. DeLuca's invention relates primarily to isolating particular muscle groups by the use of support and restraint devices which limit the movement of the patient's torso in predetermined patterns correlated to the desired muscle groups. DeLuca's electrode array consists of separate electrodes individually placed at desired locations on a patient's back.

U.S. Pat. No. 5,058,602 to Brody describes a method of electromyographic scanning of paravertebral muscles comprising measuring electrical potentials bilaterally across segments of the spine. Readings are categorized into different patterns which are indicative of different muscular conditions. Brody suggests equipment useful within his described techniques as an available EMG scanner having electrodes spaced 2.5 cm apart and a computer component, but provides few details on the equipment or an indication of usefulness for isolating certain muscles or muscle groups.

U.S. Pat. No. 5,318,039 to Kadefors, et al., describes a method and apparatus for detecting electromyographic signals, processing them and providing an indication of the change of the signal from a predetermined norm. Kadefors' electrode system comprises three electrodes, one of which is a reference marker. This electronic apparatus, in essence, includes a sample and hold function in which current responses can be compared to earlier responses and an indication provided based on the differences detected.

U.S. Pat. No. 5,505,208 to Toormin, et al., describes a method for determining the status of back muscles wherein EMG signals are monitored from a number of electrodes placed in a pattern on a patient's back, the activity of each electrode is determined and the results stored. A database of results provides a standard from which comparisons can be made to determine deviations or abnormalities, as a device for the care and management of the patient's dysfunction.

U.S. Pat. No. 5,513,651 to Cusimano, et al., describes a portable electronic instrument for monitoring muscle activity, using standard ECG electrodes and a computer for analyzing the detected signals. The electrodes are applied individually at predetermined locations and a range of motion device is employed to generate signals related to a particular muscle group. Output plots are produced to provide an indication of results, apparently in the form of printouts of information reflecting any deviations from the norm of expected muscle activity.

While the prior art devices describe much sophistication in the detection and analysis of EMG signals, there is a need for equipment which is capable of being utilized by the average skilled examining physician who, for example, uses and is familiar with the techniques of physical examination and palpation of the paraspinous musculature of the thoracolumbosacral spine.

DISCLOSURE OF INVENTION

An object of the present invention is to provide improved surface EMG equipment, readily useable by the skilled examining physician, for the diagnosis or treatment monitoring of patients with low back pain.

A further object of the present invention is to provide an improved clinical tool which is portable and which uses non-invasive techniques for the collection of signals.

A further object of the present invention is to provide improved EMG equipment which provides a visual display of the activity of muscles or muscle groups.

A further object of the present invention is to provide improved EMG equipment in which the visual display of muscle activity is juxtaposed over a visual display of normal muscle anatomy for correlation by the examining physician.

A further object of the present invention is to provide improved EMG equipment in which the visual display can be selected for specific musculature identified by the examining physician.

A further object of the present invention is to provide improved EMG equipment which utilizes a single detector pad of electrodes in which the electrodes are arranged in a specific array, to monitor instantaneously all specific muscles in a muscle group of a patient.

A further object of the present invention is to provide an improved electrode.

A further object of the present invention is to provide an improved EMG electrode which achieves better signal acquisition.

A further object of the present invention is to provide an improved electrode that is easier to manufacture.

A further object of the present invention is to provide an electrode with an ornamental design.

A further object of the present invention is to provide an improved electrode array.

A further object of the present invention is to provide an improved system for holding an electrode array in contact with a patient.

A further object of the present invention is to provide an improved method for positioning an electrode array relative to the anatomy of a patient.

A further object of the present invention is to provide an improved EMG diagnostic system which provides enhanced correspondence between collected data and the anatomy of the particular patient.

A further object of the present invention is to provide an inexpensive flexible electrode array.

A further object of the present invention is to provide an electrical connector between an electrode array and a buffer/amplifier that minimizes wear between contact points.

Further objects of the present invention will be made apparent in the following Best Modes for Carrying Out the Invention and the appended Claims.

The electromyographic (EMG) diagnostic system of the present invention is particularly suited for evaluation of the lower back of a human and consists essentially of a sensor pad for collecting and conditioning EMG signals, electronic equipment including a computer for signal discrimination and evaluation and a display device for providing a visual display of the activity of selected musculature. A ground electrode is positioned on the patient. The electronic equipment serves to receive signals from the sensor pad which is pressed against the lower back of a patient in a predetermined location and held immobile relative to the patient such as by strap with foam backing, an inflatable bladder, an adhesive pad, disposable or reusable patient adhering structures or other convenient arrangement. Signals from individual electrodes are conditioned by the electrical equipment, discriminated from noise signals and the like and evaluated relative to the signal received from the reference electrode. Computer apparatus is then used to analyze the signals, and can combine the signals in various patterns to provide an analysis of the muscular anatomy of the lower back and the activity of such muscles.

In an exemplary form of the invention electrodes are used which have a plurality of projections in either a pyramid or conical shape. The configuration enhances acquisition of signals from the underlying muscles and reduces extraneous signals produced by electrolytic and other reactions with the skin of the patient and adjacent support structures. Such electrodes are preferably arranged in an array supported on a web or pad structure. The web or pad structure is preferably flexible to conform to the contours of the patient's anatomy. The pad structure is preferably part of or connected to a releasable adhesive that adheres to the patient's skin without relative movement until removed. The supporting web or pad structure for the electrodes may be reusable or disposed of after a single use.

Alternatively, an inexpensive flexible array of electrodes is formed by depositing or printing conductive inks in the shapes of circular electrodes on a flexible and extensible substrate sheet. A flexible conductive adhesive such a hydrogel is deposited on the printed electrodes to increase the sensitivity of the electrodes and to adhere the electrodes to the skin surfaces of a patient. Trace lines are also printed on the substrate to route electrical signals from each electrode to a portion of the substrate that is operative to connect with signal processing components such as a buffer/amplifier.

One exemplary technique for signal monitoring is to determine the RMS voltage of the sensed signals over a predetermined time interval. The RMS voltage is converted to a visual display representative of the power level, which display then provides a visual indication of those locations where a higher level of muscle activity is detected. The RMS signal technique is advantageous in providing a device for averaging the highly sensitive and often variable individual electrode signals which are susceptible to changes in contact resistance at the electrode, the human skin resistance, stray field fluctuation, inadvertent movements by the patient, and the like, which can introduce false signals, and mask the desired muscle activity signals.

A visual display of the sensed muscle activity is provided on a monitor, such as a cathode ray tube type monitor, which may then be evaluated by the attending physician. A predetermined display of normal back anatomy is displayed simultaneously as an underlay on the monitor to assist the physician in his evaluation. For example colorization of the resultant sensed display with different colors representing the degree of contraction thus provides a vivid indication of abnormal activity of the muscle. The display is modified to correspond to the anatomy of the patient. Normal back anatomy is provided in this invention by the selection from an inventory of various back muscle configurations which depict different layers of back muscles of the normal human patient. These configurations are selectable by the physician for comparison with the sensed muscle activity pattern in order to assist in providing a correlation between the two. Further control is provided in that the physician not only can alter the physical configuration of the sensed signal display but also can adjust the intensity or colorization of the sensed display to render a more pronounced image of abnormal muscle activity relative to normal back anatomy. Visual display modification is achieved by adjustment of the sensitivity of the sensed signal detector or by increasing the level of signal over which a visual indication is provided.

BRIEF DESCRIPTION OF DRAWINGS

FIG. 4 is a view partly in cross-section of a portion of the sensor pad of the invention, showing a single electrode and the electrical connection to the computer portion of the invention.

FIG. 5 is an enlarged plan view only of the single electrode shown in FIG. 4.

FIG. 6 is a cross-sectional view of a single electrode taken along the lines 6—6 of FIG. 5.

FIG. 28 is a chart of a portion of the software program of the invention, showing a header format.

FIG. 29 is a chart of a portion of the software program of the invention, showing a listing of files developed therein.

FIG. 30 is a chart of a portion of the software program of the invention, showing generally the Source File Structure.

FIG. 31 is a front isometric view of an alternative electrode configuration.

FIG. 32 is a back isometric view of the alternative electrode shown in FIG. 31.

FIG. 33 is a back plan view of the alternative electrode shown in FIG. 31.

FIG. 34 is a cross sectional view of the alternative electrode taken along line 34—34 in FIG. 33.

FIG. 35 is a side view of the alternative electrode.

FIG. 36 is a front plan view of the alternative electrode.

BEST MODES FOR CARRYING OUT INVENTION

Figure 1:
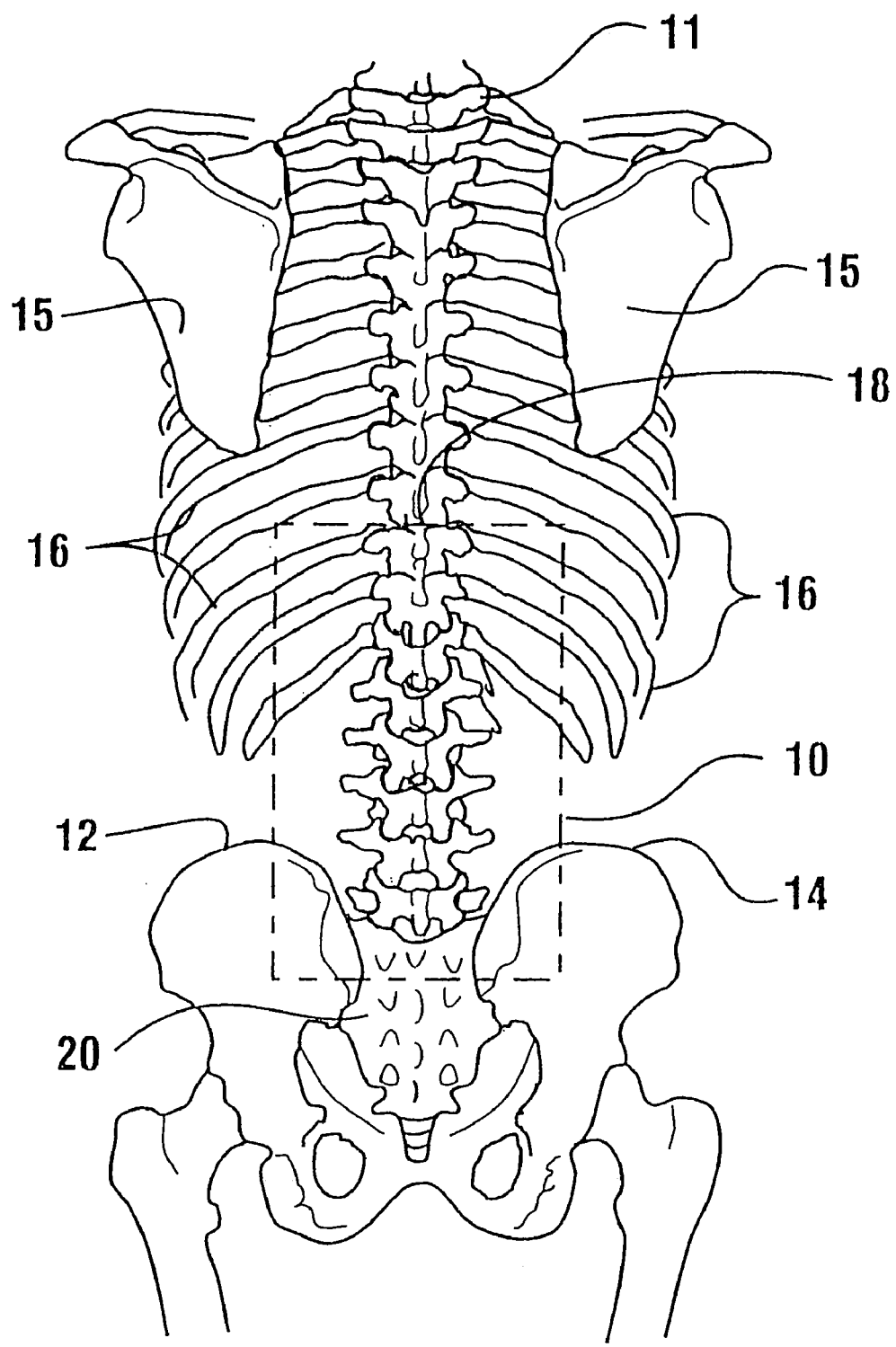
FIG. 1 is a simplified schematic overview of a portion of the lower back skeletal structure of a patient with an outline of the sensor pad portion of the invention depicted in position thereover.

Referring now to the drawings, and initially to FIG. 1, there is shown in schematic form the sensor pad 10 of the invention positioned in relation to a partial skeletal showing of the lower back of a patient, the latter comprising a spine 11, left posterior superior iliac crest 12, right posterior superior iliac crest 14, portions of the scapula 15 and ribs 16. As will be described in greater detail hereafter, sensor pad 10 is a device for collecting electromyographic (EMG) signals from the underlying muscle structure supporting and providing movement to the spine 11. The muscle structure is a complicated array of muscles consisting of at least sixty-nine erector and intrinsic muscles in the thoracolumbosacral spine extending from about the tenth thoracic vertebrae 18 to the sacrum 20. These are the primary muscles with which this invention is concerned and occur in layers from deep to superficial. Also formed in the superficial region of the lower back are several muscles which are not classical erector muscles, which while important, are not the principal interest of this invention. These latter muscles may also produce EMG signals which serve to complicate the evaluation process and may require discrimination, but which are not a primary source of the lower back pain syndrome affecting the greater portion of the patient population.

EMG signals and their relation to muscle functions are well understood at the current state of investigations. Muscles are controlled by nerves, the latter transmitting an electrical signal to a particular muscle and causing contraction thereof. The muscle itself is a volume conductor reacting to the signal of the associated nerve. There is a voltage change that occurs when a muscle contracts creating an electric potential that is directly proportional to the strength of contraction and that can be captured from the external surface area of the patient, in this instance being the surface area of the thoracolumbosacral spine. Currently, there is technology which allows certain evaluations of the electrical activity of muscles such as EMGs or EKGs and which may be displayed in analog, waveform or spectral forms. Available technology and the associated devices however are deficient in not being able to select all muscles in a muscle region in a manner which is conducive to evaluation by an attending physician.

Figure 2:
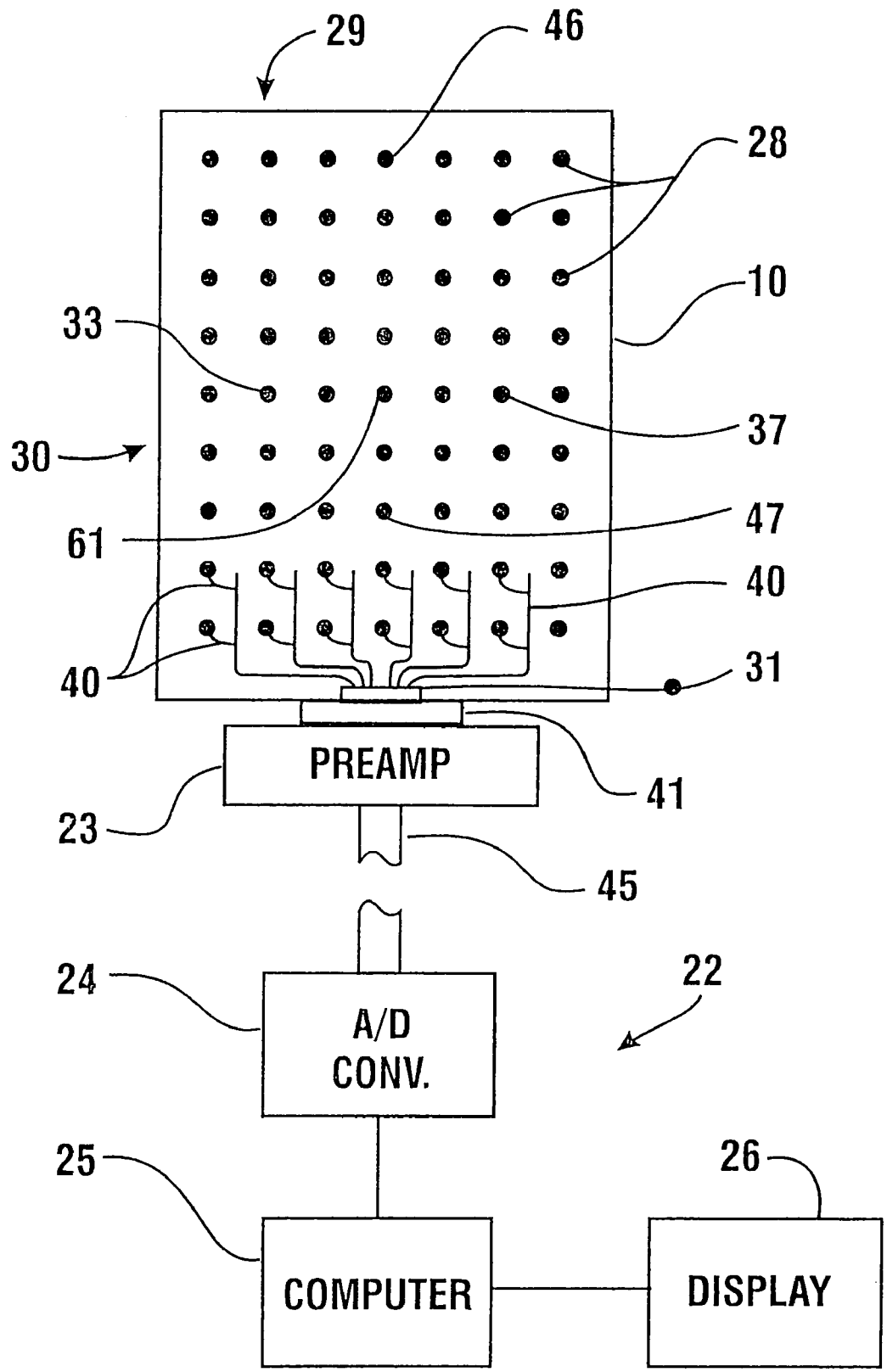
FIG. 2 is a schematic view of the apparatus of the invention, comprising the sensor pad in connection with electronic apparatus including a computer and display unit.

Referring now to FIG. 2 there is shown in schematic form, the essential elements of this invention as comprising sensor pad 10 and electronic apparatus 22 comprising preamplifier 23, converter 24, computer 25 and display unit 26. Sensor pad 10 in a first embodiment is a flat rectangular piece of siliconized rubber, approximately 0.157 cm (0.062 inch) thick, measuring about 30.48×30.48 cm (12×12 inches) and with a Durometer hardness on the order of 20 to 40. One source for sensor pad 10 is Fairprene Industrial Products, Inc. of Fairfield, Conn.

Sensor pad 10 further comprises an array of sixty-three electrodes 28, which may be made of 316 L stainless steel, silver or other materials. Electrodes 28 are preferably arranged in a 7×9 pattern, with the electrodes in each row and column being spaced 2.95 cm (1.162 inches) apart on center. A central column 29 of nine electrodes 28 is located in the middle of sensor pad 10 to overlay the spine 11 of the patient, and three equally spaced parallel columns of nine electrodes each are positioned on either side of the central column 29. Similarly, a central row 30 of seven electrodes 28 is positioned near the center of sensor pad 10, and four parallel rows of seven electrodes each are positioned on either side of central row 30. Ground electrode 31, is a standard electrode preferably positioned on a wrist of the patient. Of course in other embodiments other configurations may be used.

All of the electrodes 28, are preferably identical and one configuration is shown in greater detail in FIGS. 4–6 as comprising a pyramidal tipped, bolt-shaped structure having a head 32 and integral threaded shaft 34. Head 32 is circular and includes a plurality of pyramids 35 distributed substantially evenly and projecting outwardly of the upper surface of head 32 to form the patient-contacting surface of electrode 28. Head 32 is preferably about 0.95 cm (0.375 inches) in diameter and has a thickness of about 0.20 cm (0.08 inches) from the lower surface thereof at the junction with shaft 34, to the tips 36 of pyramids 35. Pyramids 35 are formed by grinding electrode head 32 in a series of parallel and orthogonal passes or by electromachining to produce a square pyramidal shape having an altitude of about 0.107 cm (0.042 inches), an angle of about 90 degrees between opposing pyramid faces and culminating in a tip 36 having a radius of about 0.0127 cm (0.005 inch). Tips 36 are spaced about 0.2387 cm (0.094 inches) from one another and in this embodiment of the invention, result in an electrode 28 having twelve pyramids 35 and tips 36 at the signal-collecting surface thereof. It has been determined that this configuration of electrode 28 is useful in enhancing lower contact resistance when placed in position on a patient, thereby assuring better EMG signal reception and greater accuracy of the measurement.

Each electrode 28 is mounted in an aperture in sensor pad 10 and retained in position by a nut 170 threaded to shaft 34. Alternatively, electrode 28 may have an unthreaded shaft 34 and be retained in position by a push connector. A solderless ring connector 38 is also received on shaft 34 and is firmly secured by outer nut 39 to provide an electrical interconnection with the signal gathering surface of electrode 28. An electrode wire 40 is crimped to connector 38 and each of the electrode wires 40 is routed over the surface of sensor pad 10 to a pigtail at the upper end of sensor pad 10 which terminates at a connector 41. Each electrode wire 40 is preferably a 30 gauge, multi strand, flexible copper wire which allows for some deformation of sensor pad 10 to conform to the lower back of a patient, while connector 41 allows for releasable connection of the sensor pad to the electrical circuitry to facilitate substitution of components of the apparatus of the invention. With an electrode head 32 diameter and spacing, as mentioned in the described embodiment, the edge to edge spacing of electrodes 28 in each column 29 and row 30 is about 2.0 cm (0.79 inches). This has been determined to provide enough distance between electrodes 28 to result in a meaningful signal difference between electrodes. Electrode 28 may also be used in connection with the reusable or disposable self adhesive sensor pads which are later discussed in detail.

An alternative electrode 200 used in connection with embodiments of the EMG diagnostic system of the invention are shown in FIGS. 31–36. Electrode 200 includes a head portion 202 and a stem portion 204. The stem portion is suitable for electrical connection with electrode wires in a manner similar to the previously described embodiment.

The head portion of the electrode 200 includes a base surface 206 and a plurality of conical projections 208 extending forward therefrom. The conical projections 208 in one exemplary embodiment are comprised of nested circular arrangements of six cones each. A first set 210 of six cones is spaced in close relation about a central projection 212. A second set 214 of six cones is spaced in outward nested relation relative to the first set 210. A third set 216 is disposed outwardly relative to the second set 214. Each of the cones in the third set 216 are spaced in nested relation between cones in the second set. In the exemplary form of the invention each of the cones are arranged concentrically about the central projection 212 as shown in FIG. 36.

In one embodiment of the alternative electrode 200 the base surface is approximately 1.066 cm (0.420 inches) in diameter and the stem portion is approximately 0.318 cm (0.125 inches) in diameter. In this embodiment the first set of conical projections is spaced in a circle of about 0.391 cm (0.154 inches) in diameter. The second set of six cones is spaced on a circle about 0.678 cm (0.267 inches) in diameter and the third set of cones is spaced on a circle about 0.782 cm (0.308 inches) in diameter. Of course in other embodiments other configurations may be used.

The exemplary configuration of the conical projections provides for the projections to extend about 0.071 cm (0.028 inches) above the base surface. The incident angles of the walls bounding the cone extend at an angle C as shown in FIG. 34 which is about 79 degrees. The tips of the cones are rounded and have radii of about 0.0127 cm (0.005 inches). The thickness of the electrode 200 underlying the base surface is generally about 0.053 cm (0.021 inches). Of course in other embodiments other configurations may be used.

In the exemplary form of alternative electrode 200 the electrode is comprised of an ABS carbon-composite resin material. The ABS resin is preferably provided with a coating of a suitable conductive material which in the exemplary form of the electrode is a silver/silver chloride material. The coating is preferably deposited on the ABS resin body by electroplating, vacuum metalization or similar processes. In alternative embodiments other approaches may be used.

A useful aspect of the described embodiment of the alternative electrode 200 is that the plated electrode contacts the patient's skin with a material that has a minimal electrolytic reaction with the skin of the patient. This minimizes, the electrolytic currents which are produced as a result of contact and produces improved signals. In addition the arrangement of nested conical surfaces provides a relatively larger surface area for contact with the skin. The conical projections extend inward relative to the normal contour of the skin to provide signal acquisition from this area. This further enhances the ability of the electrode to acquire signals produced by the underlying anatomy. The structure of the exemplary form of the alternative electrode is also economical and may be produced using cost effective manufacturing processes. Further the exemplary form of the electrode provides an attractive and ornamental design.

The electronic circuitry comprising preamplifier 23 is located near sensor pad 10 for conditioning and amplifying the signals received at electrodes 28. Electrode wire 40 is connected to buffer amplifier 42, and the signal in turn is routed to low pass filter 43 and high pass filter 44 for each electrode 28 of sensor pad 10. Conditioning of the signals preferably occurs closely adjacent the patient and avoids remote transmission of very low level signals in a background of randomly generated noise signals. Buffer amplifier 42 minimizes leakage current through the electrode and errors due to electrode impedance changes. High pass filter 44 serves as an anti-aliasing filter, and low pass filter 43 prevents saturation of analog to digital (A/D) converter 24 by offset voltages, such filters being well understood in the art.

Figure 24:
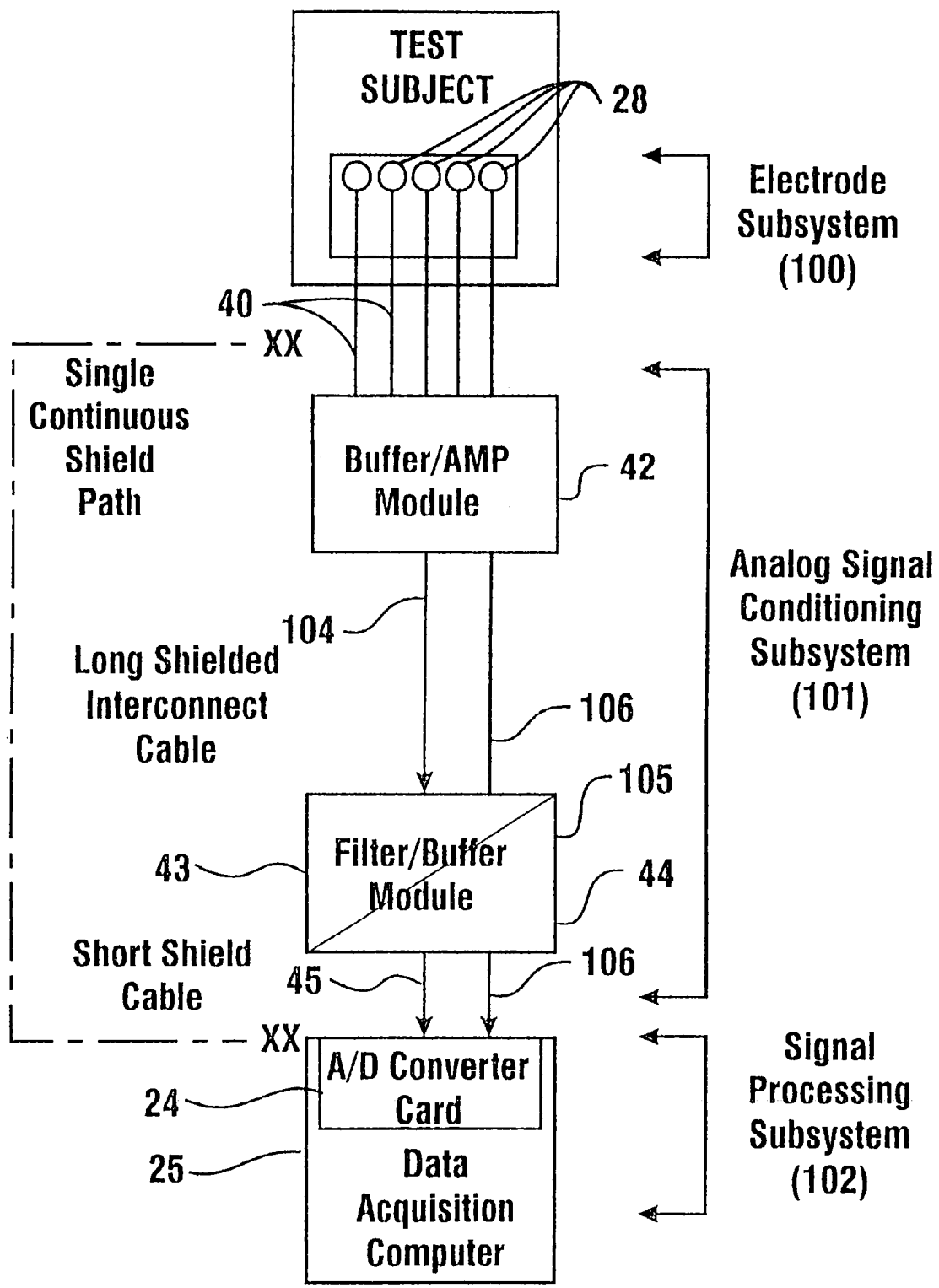
FIG. 24 is a schematic view of the apparatus of the invention, similar to that of FIGS. 2 and 4, in a modified showing of the interrelation of components of the invention.

As shown in FIG. 24 preamplifier 23 includes Buffer/Amplifier module 42 and Filter/Buffer module 105. Cable 45 connects the components of preamplifier 23 to analog to digital (A/D) converter 24 for transmission of the electrode signals for further processing and analysis.

Sensor pad 10 is applied to the back of a patient by orienting certain of the electrodes 28 to the skeletal structure of the patient. In one embodiment central electrode in the top row of electrode rows 30, i.e., electrode 46 is located over the spinous process of the tenth thoracic vertebrae 18. Two other landmarks are identified in a similar manner as the sensor pad 10 overlays the mid portion of the posterior superior iliac crest (PSIS). For example, the second and sixth electrodes 33, 37 respectively, in the center row of electrode rows 30 may be over the left PSIS and right PSIS. Alternatively, other landmarks may be used, such as an electrode overlying the fourth lumbar vertebrae, or other physiological reference point. This calibration information is then fed into the electronic apparatus 22 for appropriate adjustment of the voltage data received from electrodes 28 and subsequent visual display relative to predetermined displays of muscular anatomy appearing at display unit 26, in order to assure standardization of electrode placement.

In alternative forms of the invention an alternative protocol may be used for positioning and locating the electrode array. Such methods may be used in connection with sensor pad 10 as well as the reusable and self adhesive sensor pads later discussed.

Locating of the sensor pad begins with the patient in a neutral upright position. The patient's feet are preferably shoulder width apart, the head and face forward. The clinician positioning the electrode array may palpate both the left and right superior iliac crests to locate their position. Drawing an imaginary line directly between these two points, the clinician palpates the spinous process at this level which is L4 the fourth lumbar vertebrae. The clinician then marks the L4 spinous process with a water soluble marker. The electrode positioned in the middle column and seven rows from the top is then positioned directly over the L4 indicator. This electrode is marked 47 in FIG. 2.

Continuing with the location and calibration process, once the L4 electrode has been positioned the clinician palpates the most inferior point of the inferior angles of both scapulae. The clinician then envisions an imaginary line between these two points and palpates the spinous process at this level. This is the seventh thoracic vertebrae T7. The clinician may then use calipers or other suitable measuring device for measuring from the T7 spinous process to electrode 47 at L4. This measurement may be recorded, or in some embodiments input to the computer through an input device for correlating the output to the dimensions of the patient's anatomy in a manner that is later discussed.

Continuing with the protocol, with the patient in the same position the clinician finds the left superior iliac crest at its most lateral point. Using calipers or other measuring device the clinician measures from the most lateral aspect of the left iliac crest to the electrode at L4. This measurement is also recorded or in some embodiments input to the computer through an input device.

In some embodiments of the invention the computer 25 includes software which is operative to scale outputs displayed responsive to the configuration of the patient's anatomy. This is achieved because the dimensions of the patient are known as are the distances between the electrodes. In this manner the computer is enabled to calculate or otherwise determine how the anatomical features underlying the electrodes correspond to the electrode positions for the given dimensional configuration of the patient. This enables signals from electrodes to be more accurately correlated to underlying anatomical structures, such as muscles which are exhibiting spasmodic conditions.

Figure 8:
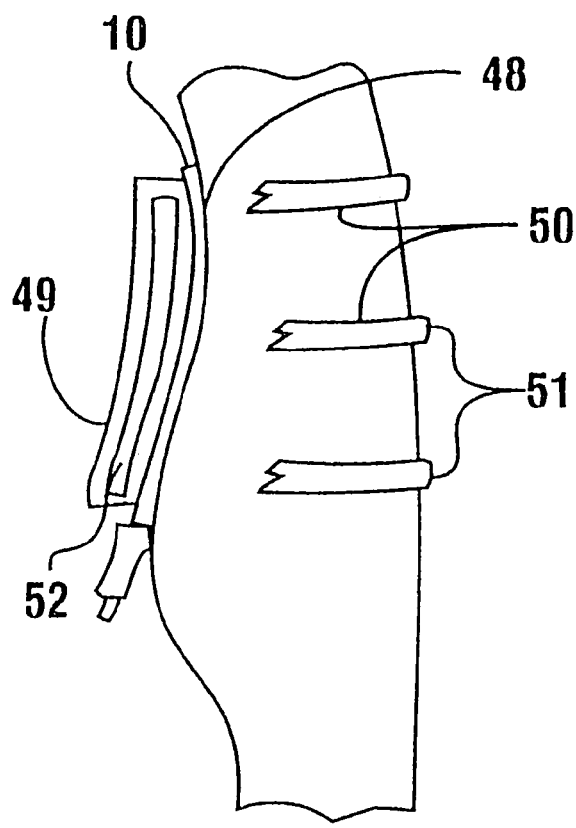
FIG. 8 is a schematic view of the lower torso of a patient with the sensor pad held in position by a retaining belt and a support pad.
Figure 9:
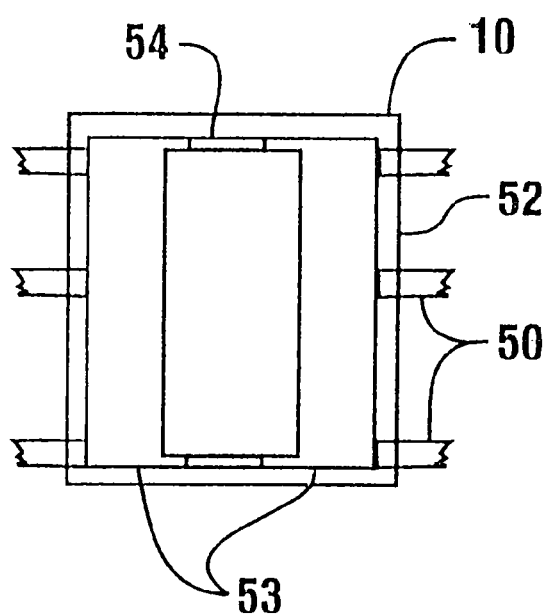
FIG. 9 is a plan view with parts removed of the retaining belt of FIG. 8, showing the support pad.

Referring now as well to FIGS. 8 and 9, there is shown in too views the mechanism for attachment of sensor pad 10 to the lower back of a human patient 48. A type of lumbar support belt 49 encircles part of the lower torso of patient 48 and is retained in place by several straps 50 of non-elastic web culminating in quick release snaps 51 at the ends thereof for adjustment and securement. Belt 49 includes a pouch therein in which is disposed a molded foam pad 52. Pad 52 is generally rectangular in configuration and about 2.54 cm (one inch) in thickness at its midpoint and tapering to about 0.3175 cm (0.125 inch) thickness at its left and right edges. The pad has a curved inner surface generally conforming to the curvature of the lower torso of a typical patient 48 and overlying sensor pad 10 to press the latter into secure physical contact with patient 48 as straps 50 are adjusted. Preferably, belt 49 is about five cm (two inches) larger than the operative portion of sensor pad 10, and pad 52 is also slightly larger than sensor pad 10, thereby to overlap the latter and assure fairly uniform pressure over the entire area of sensor pad 10 and consistent readings from electrodes 28.

Preferably, pad 52 has three parts, namely parallel vertical sections 53 and a central stiffer section 54. Pad 52 is firm, yet flexible, and thicker in the central section 54 than in the outer sections 53 as described above. In this manner a better fit is made to accommodate the contour of the human back. Support belt 49 is preferably made of non-elastic nylon material as are straps 50 to achieve a secure and reliable connection to the patient 48.

Preferably, a conductive gel is applied to electrodes 28 (or alternative electrodes 200) to enhance conductivity of the interface between electrodes and patient 48, as is well known in the art. One suitable brand of water soluble gel is that manufactured by TECA, a subsidiary of Vickers Medical, Inc. Alternative approaches to locating and securing the electrodes to a patient may be used. For example FIG. 37 discloses a disposable sensor supporting pad or sheet generally indicated 220. Sensor supporting sheet 220 comprises a flexible web material that is relatively thin and sufficiently flexible to conform to the contours of the patient. As shown in FIG. 38 web material 222 includes apertures 224 therethrough. Apertures 224 are sized for accepting the head portions of electrodes designated 226 therethrough. The electrodes may be of the type described herein or other types. For example when electrodes 200 are used the apertures 224 are sized such that the head portion of the electrode is enabled to contact the skin of the patient in the area of the conical portions 208. The front face 228 of the web material 222 preferably includes an adhesive thereon. The adhesive is preferably made to adhere to the skin of the patient once adjacent thereto, but may be released from the skin in response to a less than harmful removal force. The adhesive material applied on the front face is preferably sufficiently strong once adhered to prevent relative movement of the electrodes on the skin of the patient until the web material is removed by a clinician. The adhesive material on the front face 228 is preferably covered by a separable cover sheet which covers the adhesive material until the sensor supporting sheet is ready to be applied to a patient.

Figure 37:
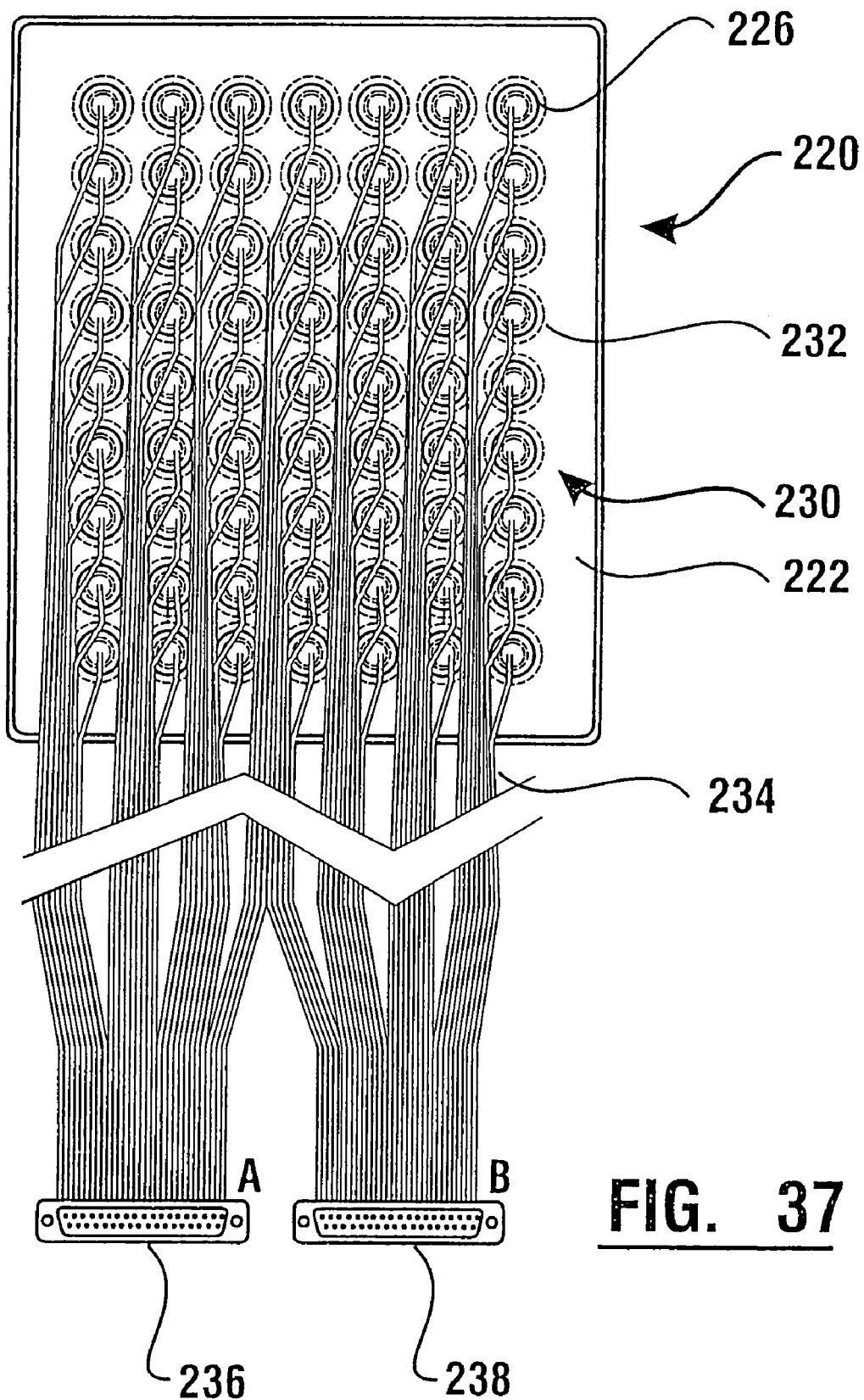
FIG. 37 is a rear plan view of an electrode array and self adhesive electrode support pad.
Figure 38:
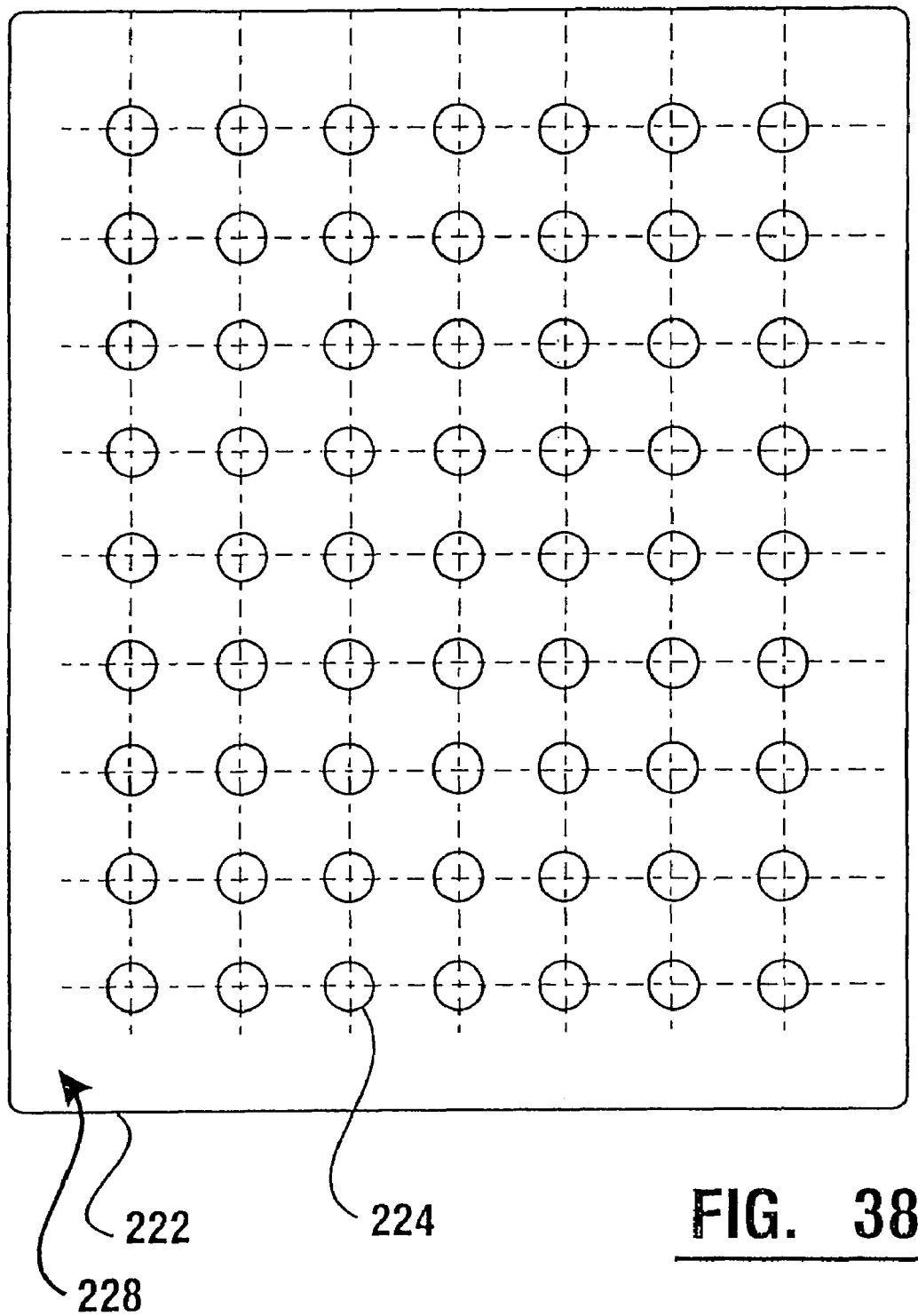
FIG. 38 is a front plan view of the self adhesive support pad shown in FIG. 37 without electrodes mounted thereon.

As shown in FIG. 37 the electrodes 226 are held to a rear face 230 of the web material 222. This is accomplished in the embodiment shown by support discs 232. Support discs 232 are preferably flexible sheet material with an adhesive or similar flexible attaching means thereon which adhere to both the electrodes and the rear face 230. The support discs include an opening therethrough which enables wires or other electrically conducting elements 234 to extend therethrough to contact the electrodes. It should be understood that while electrical wires are shown in the embodiment described in connection with FIG. 37, in other embodiments other types of electrical conductors such as electrical trace conductors or other types of conducting means may be used. As shown in FIG. 37 the wires 234 terminate at electrical connectors 236 and 238. The electrical connectors are adapted to connect the wires and the associated electrodes to the remainder of the system.

The disposable electrode array which includes sensor supporting sheet 220 is useful because it is sufficiently flexible to conform to the contours of a patient's anatomy. Further the adhesive material secures the electrode in contact with the patient's skin and generally prevents relative movement until the sensor array is ready to be removed. The disposable character of the sensor supporting sheet also reduces time associated with cleaning components between patients. The components of the system are preferably assembled in a manner that enables the wires and electrodes to be readily disconnected, cleaned and recycled into new sensor supporting sheets.

Figure 39:
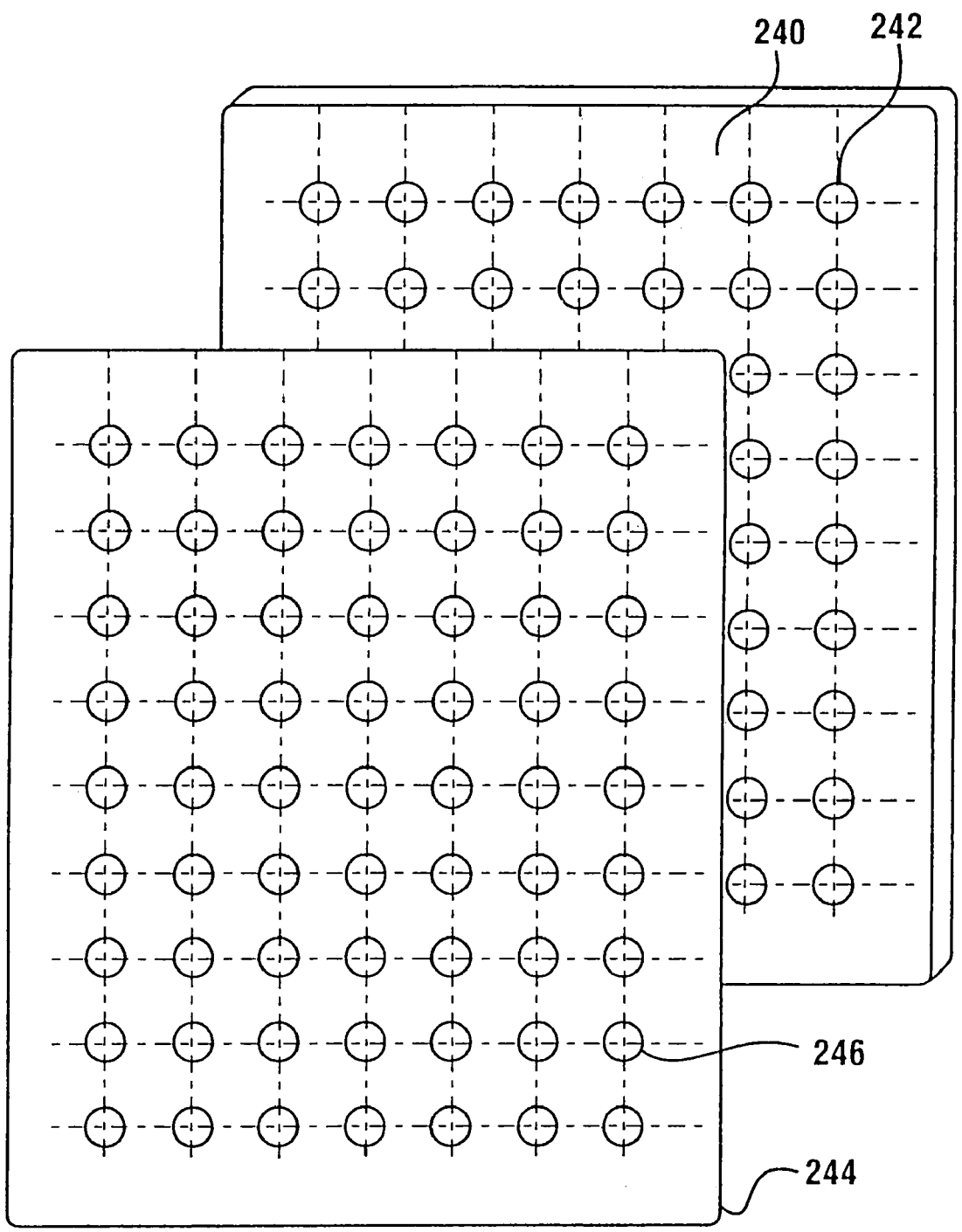
FIG. 39 is an isometric view of a reusable electrode support pad and removable adhesive web for use in connection with the reusable electrode support pad.

An alternative configuration for supporting an electrode array is shown in FIG. 39. In the embodiment shown in FIG. 39 the electrodes are supported on a flexible resilient pad 240. Pad 240 is preferably comprised of silicone or other material sufficiently flexible to conform to the contours of a patient's body. Electrodes designated 242 are positioned in supporting connection with the pad. Electrodes 242 may be mounted in apertures that extend through the pad 240 in some embodiments. Alternatively electrodes 242 may be in molded connection with the pad. In addition the wires which extend to the electrodes 242 may also be molded into the pad to facilitate connection to the electrodes and to minimize the risk of damage.

A double stick adhesive web or sheet 244 is positioned adjacent to pad 240. Adhesive sheet 244 includes apertures 246 that extend therethrough. The positions of apertures correspond to the positions of electrodes 242 such that the heads of the electrodes may extend therethrough. Adhesive sheet 244 includes adhesive on the side adjacent to the pad 240 which serves to adhere to the adhesive sheet thereto. However the nature of the adhesive and the sheet material is such that the adhesive sheet once adhered to the underlying pad may be removed therefrom without damaging the pad or the electrodes.

The adhesive sheet 244 further includes an adhesive material on the side opposite the pad 240. This adhesive material is suitable for adhering the sheet 244 and the attached pad 240 to the skin of the patient in a manner similar to the sensor supporting sheet 220. The adhesive sheet 244 preferably includes a reversable cover sheet or similar item attached to the patient side thereof to maintain the adhesive generally dirt free until the sheet is ready to be adhered to the back of the patient. When the pad 240 is ready to be brought into contact with the patient's back the sheet covering the adhesive on the patient's side of sheet 244 may be removed. The pad 240 may then be positioned and conformed to the contours of the patient and the signals from the electrodes may then be analyzed as later discussed. When the analysis and other activities are complete the pad 240 and sheet 244 may be removed from the patient's back.

A useful aspect of the structure shown in FIG. 39 is that the adhesive sheet will generally absorb the dirt, hair and other material collected from the patient. After use the sheet 244 may be separated from the adhesive pad 240. The surfaces of the electrodes may then be cleaned and the pad made ready for reuse. The ability to collect hair and other material on the disposable adhesive sheet 244 reduces the time required for cleaning the electrodes and pads. Of course in other embodiments of the invention other approaches may be used.

Figure 40:
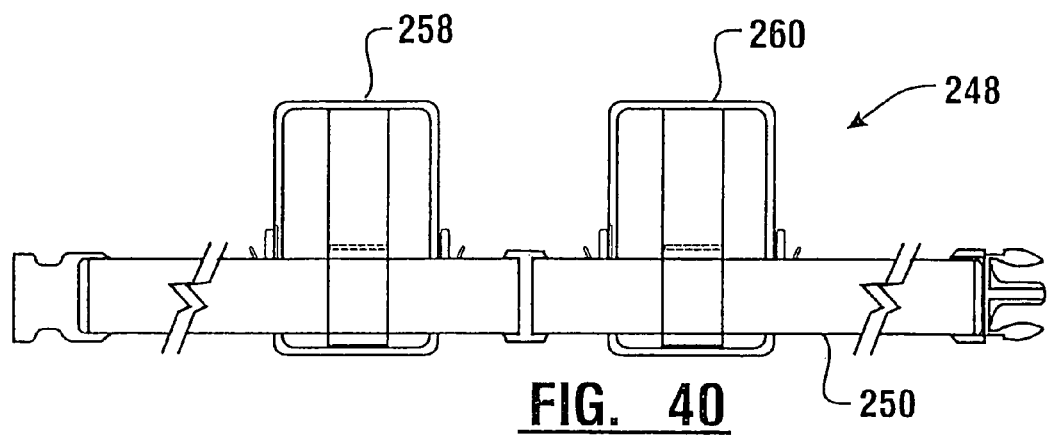
FIGS. 40, 41 and 42 are back, top and front views respectively, of the electrical component holster supporting belt worn by a patient in connection with self adhesive electrode array supporting pads.
Figure 41:
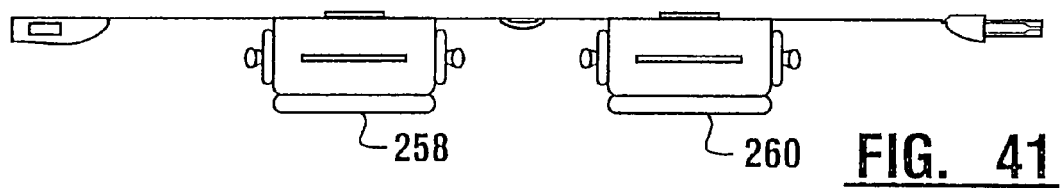
Figure 42:
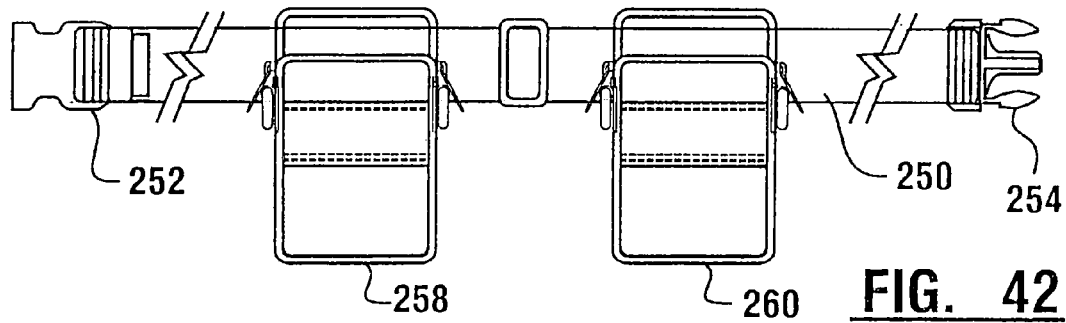

When the electrode arrays shown in FIGS. 37 and 39 are used there is generally no location on the structure supporting the electrode array to mount the electronics components for amplifying and conditioning the signals which are derived from the electrodes. As previously discussed, it is advisable to condition and/or amplify such signals as close to the source as reasonably possible to avoid the introduction of extraneous signals. To achieve this goal the holster and belt combination designated 248 and shown in FIGS. 40–42 is used. Holster belt 248 includes an adjustable belt portion 250 which can be sized to be supported around a suitable area of the patient. In most cases this will be the patient's waist or hips. A quick release buckle or a reversable snap including a first end 252 and a cooperating second end 254 are attached to the belt portion.

A first pocket 258 and a second pocket 260 are supported on the belt portion 250. Each of the pockets preferably includes electrical connectors which provide an electrical connection with connectors from the electrode array such as connectors 236 and 238 shown in FIG. 37. Pockets 258 and 260 also preferably include electrical signal conditioning components which are desirable to place adjacent to the patient. This may include for example the preamplifiers and other signal generating or conditioning circuitry for conditioning the electrode signals. Pockets 258 and 260 may also include further connectors for outputting the conditional electrical signals therefrom.

It should be understood that the described form of the holster belt 248 is exemplary and in other embodiments other approaches to supporting the electrical connectors and signal conditioning components may be used. These may include for example supporting such components on other structures supported by the patient or on other types of support structures which are not supported by the patient.

Figure 43:
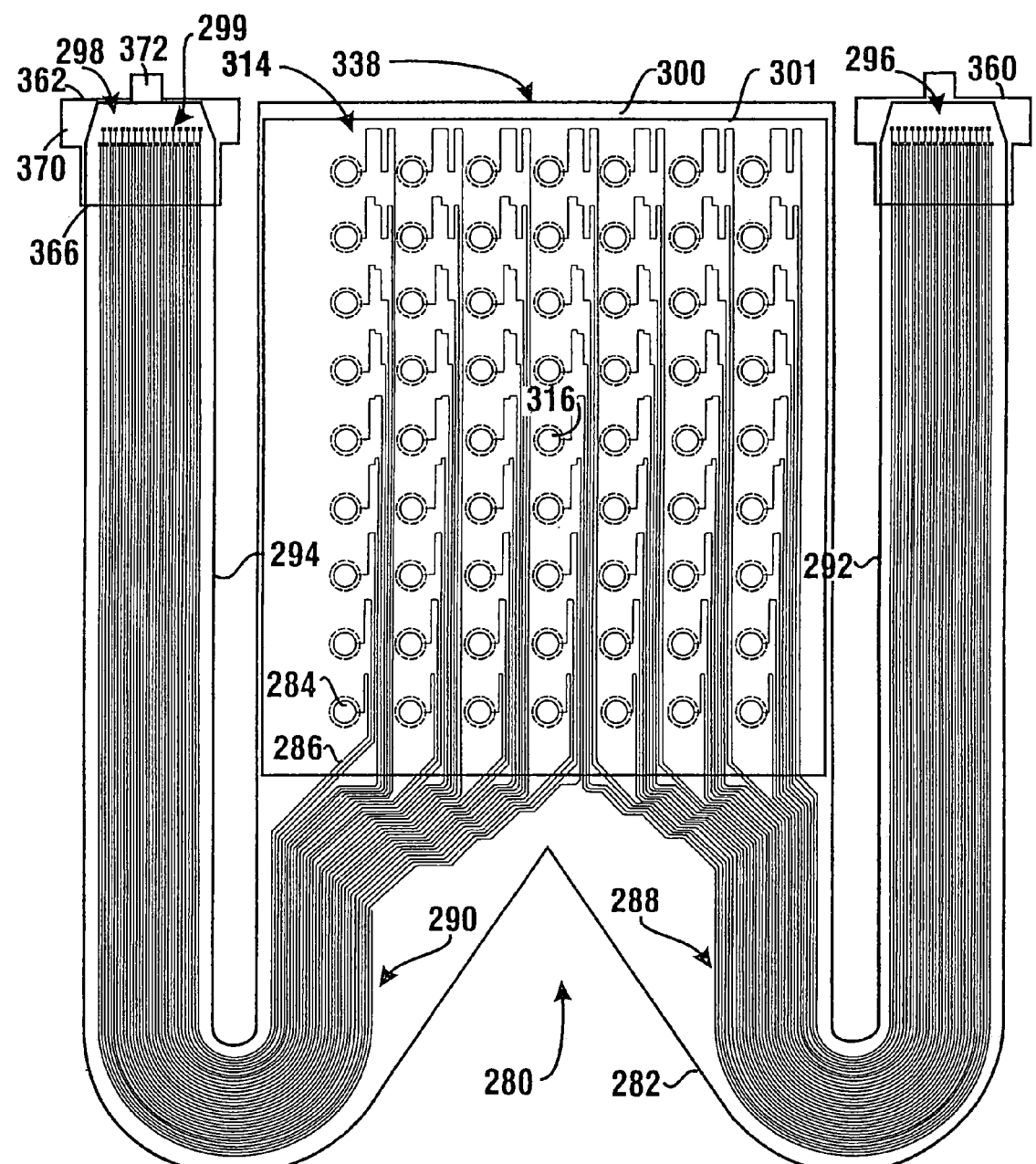
FIG. 43 schematically represents an exemplary embodiment of a flexible electrode array.

FIG. 43 schematically represents an alternative exemplary embodiment of the electrode array 280. Here both the electrodes 284 and electrical traces 286 are formed by depositing or printing electrically conductive inks on a flexible non electrically conductive substrate 282. In this described exemplary embodiment the substrate 282 is a sheet of polyester such as Mylar®; however, in other embodiments other flexible materials that are operative to support conductive materials may be used.

A plurality of the electrodes 284 are printed on the substrate 282 in a predetermined pattern. In this described exemplary embodiment the electrodes 284 are printed in uniform array 314 of nine by seven electrodes. Each electrode is printed in the shape of a solid circle with a diameter of about 1.27 cm (0.5 inches). However, in other embodiments other sizes, shapes, and patterns of electrodes can be printed based on the desired sensitivity and intended use for the flexible electrode array. Other examples of possible electrode shapes include hexagons and stars.

At lease one trace is printed on the substrate 282 for every electrode. The traces are printed in a pattern such that the traces are in electrical connection with the electrodes. The traces then converge into two groupings 288 and 290 of parallel trace lines. In this described exemplary embodiment the substrate is cut to include two long tails 292 and 294. The groupings of parallel traces 288 and 290 are printed along the tails 292 and 294 and terminate at connection ends 296 and 298. The connection ends are printed in a pattern that is operative to mate with an external electrical connector such as the Zero Insertion Force (ZIF) connector discussed later in detail. For this described exemplary embodiment the center electrode 316 is used as a reference electrode and may be connected to one or more additional trace lines.

When in use with the computerized EMG diagnostic system, the mid section 300 of the flexible electrode array is placed against the back of a patient. The tails 292 and 294 have sufficient length and flexibility to wrap around the torso of the patient and to connect to additional conditioning circuitry such as buffer/amplifiers. The additional circuitry may be located in the pouch of a holster belt as discussed previously or may be connected to a belt with a clip or other attachment device such as snaps or velcro.

Figure 44:
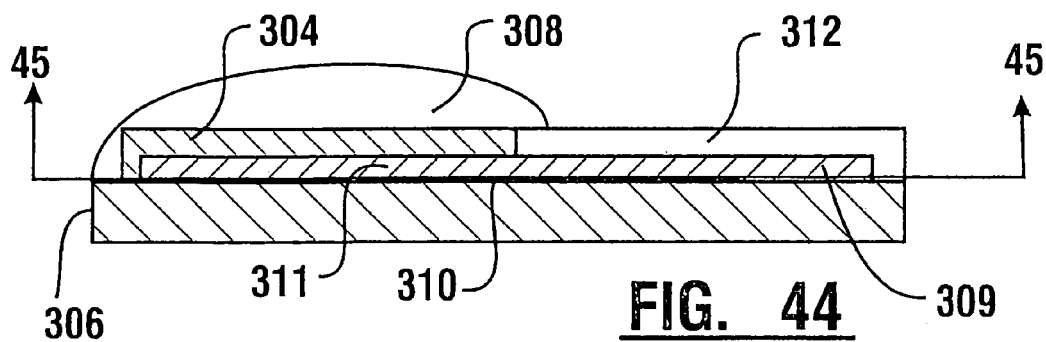
FIG. 44 is representative of a cross sectional side view of the deposited materials comprising the flexible electrode array

FIG. 44 is representative of a cross sectional view of the flexible electrode array 302. In this described exemplary embodiment each electrode 304 is silk screen printed oh the substrate 306 with a highly conductive printing material such as a silver/silver chloride epoxy ink. A conductive self supporting adhesive 308 such as hydrogel is stenciled over each printed electrode and UV cured in place. In alternative embodiments the hydrogel can be cured by other means including thermal curing. The hydrogel provides additional electrical conductivity between the surface of a patient's back and the printed electrode. In addition the hydrogel enables each printed electrode to adhere to a patient's back with sufficient adhesive strength to support the flexible electrode array in place.

Figure 45:
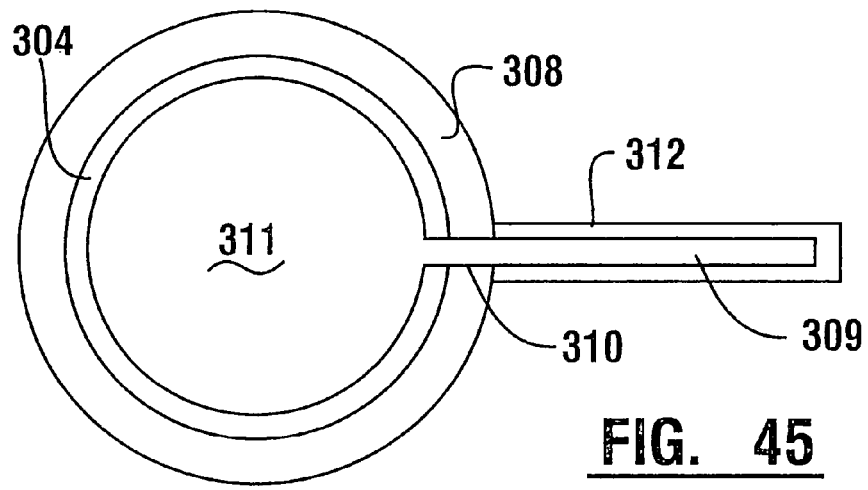
FIG. 45 is representative of a cross sectional bottom view of the deposited materials comprising the flexible electrode array.

In this described exemplary embodiment, traces 310 are silk screen printed on the substrate 306 with a silver epoxy ink 310. As shown in the cross-sectional bottom view of FIG. 45, each trace 310 includes a circular end 311. The silver/silver chloride epoxy ink of the electrode 304 is printed over the silver epoxy circular end 311 of the trace 310 to provide a strong electrical connection between the electrode and the trace deposits.

In addition, the more narrower trace line portions 309 of the traces 310 are insulated by printing additional layers of a non conductive ink 312 over the trace lines 309. In this described exemplary embodiment each conductive trace line is about 0.05 cm (0.02 inches) in width. The insulating ink line is centered over each conductive trace line and has a width of about 0.2 cm (0.08 inches). In alternative embodiments trace lines 309 may have variable widths so that the impedance of each trace is the same, even though the trace lines have different lengths.

Although in this described embodiment the electrodes and traces are silk screened on a substrate, in alternative embodiments, the flexible electrode array can be produced by any process that is operative to deposit or print a specifically defined pattern of conductive materials on a flexible sheet. Examples of such other processes includes flexographic printing with conductive inks. In other embodiments subtractive methods can be used such as chemical etching of aluminum or copper on clear polyester.

In addition, rather than insulating trace lines with non conductive inks, other embodiments may include a non conductive overlay sheet for insulating the printed trace lines. Such an overlay would leave the electrodes and connector ends exposed by including a plurality of apertures in the overlay which coincide with the printed electrodes and connector ends.

One advantage of printing both the electrode and the traces on a clear flexible plastic substrate such as polyester sheet is the reduction in the cost associated with manufacturing the flexible electrode array. The lower cost enables the flexible electrode array to become a disposable part in the computerized EMG diagnostic system; thus, eliminating the need to clean electrodes between uses of the system. In addition, using a transparent substrate such as a polyester sheet, aids in the accurate positioning of the electrodes by allowing a clinician to see the underlying anatomy of the patient through the flexible electrode array. Thus, after a clinician has marked the locations of vertebra on a patients back, the clinician can precisely position the center column of the printed electrodes over these markings.

Another advantage of using a polyester substrate such as Mylar®, is that polyester film is a material that is both tear resistant and sufficiently flexible to conform to the general shape of a patient's back. Further, the present invention achieves increased flexibility and extensibility in the design of the flexible electrode array by including a plurality of strategic slits in the substrate to make the flexible electrode array extensible (stretchy) in between electrodes. This enables the flexible electrode array to stretch or compress in three directions (horizontal, vertical, and diagonal).

Figure 46:
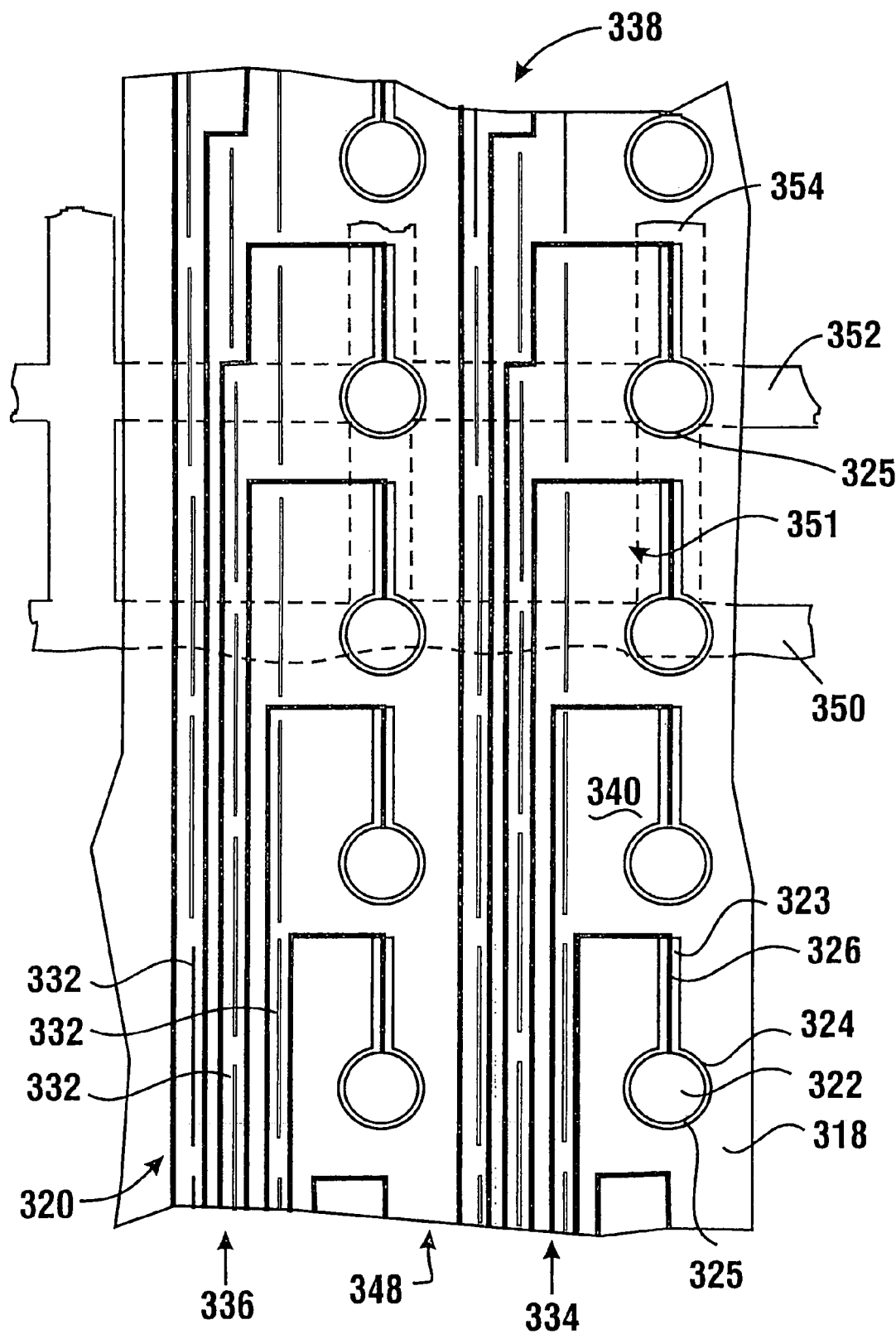
FIG. 46 schematically represents a portion of the flexible electrode array with a plurality of printed electrodes and trace lines with strategically cut perforations in the substrate for enhancing flexibility and extensibility of the electrode array.

FIG. 46 is representative of a portion of a flexible electrode array 320. In this exemplary embodiment of the array, the substrate 318 is strategically cut to include a plurality of cuts or perforations 324 through the substrate that are located along the outside perimeter of each printed electrode 322. In the exemplary embodiment the perforations extend through the substrate. However, in alternative embodiments, the perforations need not go all the way through the substrate.

Figure 47:
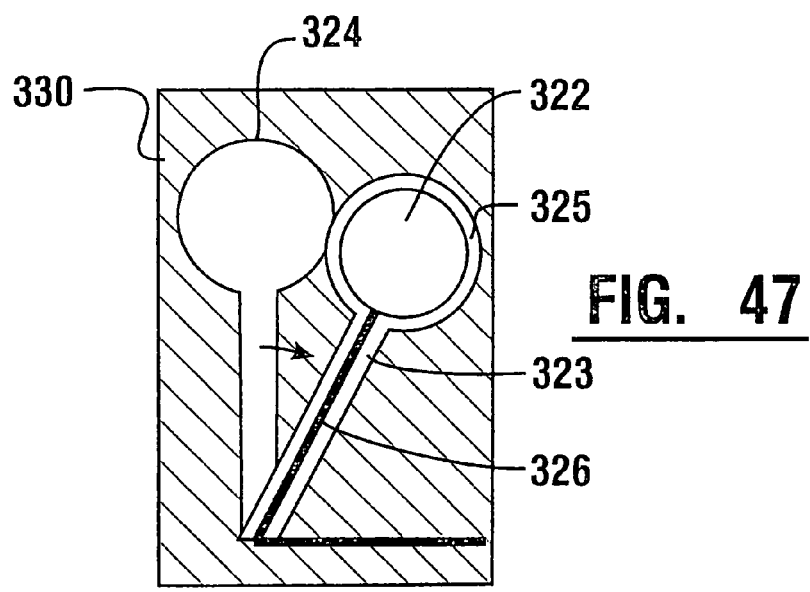
FIG. 47 is representative of a top plan view of the electrode array with the printed electrode flexing away from its original position cut in the substrate.

These perforations 324 also extend along each trace 326 adjacent an electrode 322 to form a stem portion 323 of the substrate that supports each trace. These perforations enable each printed electrode 322 and the electrode supporting portion of the substrate 325 to move in a plurality of directions with respect to the rest of the substrate 340, while remaining in electrical communication with the remainder of the electrode array. For example FIG. 47 shows a top perspective view of the printed electrode 322 and the electrode supporting portion of the substrate 325 that has been bent or flexed away from the perforation 324 in the supporting substrate 330.

When the entire flexible electrode array is placed on a patient's back, each electrode adheres to the skin of the patient's back. As the patient moves into different positions, the printed electrodes are operative to move with respect to each other in response to the patient's back muscles stretching or contracting.

Referring back to FIG. 46, this described exemplary embodiment also includes additional parallel perforations 332 in the substrate. These slits are grouped into a plurality of sets 334 and 336 which extend along the entire length of the substrate. These parallel perforations enable the substrate to stretch in one or more directions with the movement of a patient's back. Along with the perforations 324 around the individual electrodes, these parallel perforations 332 further enable the flexible electrode array to stretch or flex responsive to movement of back muscles, without individual electrodes being pulled away from their original positions on the patient's back.

As shown in FIG. 43, this described exemplary embodiment of the flexible electrode is protected by a removable cover sheet 301 that is placed on top of the array of printed electrodes 314. The hydrogel is sufficiently sticky to support the removable cover sheet 301 in place prior to the flexible electrode array being used. To separate the removable cover sheet 301 from the underlying array of electrodes 314, the cover sheet is typically peeled away from the flexible electrode array starting at the top 338 of the flexible electrode array.

As shown in FIG. 46 the perforations are located around the electrode 322 and trace 326 such that the stem portions 323 of the substrate are oriented in a common direction. One advantage of this particular pattern, is that when the removable cover sheet 301 is pealed away starting at the bottom 338 of the flexible electrode array 320, the printed electrodes will not be pulled away from the base substrate 340 at an odd angle which may tear the electrode supporting portion 325 and/or stem portion 323 from the remaining portions of the substrate 340.

This described embodiment of the flexible electrode array also encompasses a release sheet adhesively attached to the substrate on the side opposite the previously described cover sheet 301. As shown in FIG. 46, the release sheet 350 includes a plurality of rectangular apertures 351 which result in the release sheet having of a grid pattern with a plurality of rows 352 and columns 354. The rows and columns are positioned along the release sheet 350 to intersect with the electrode supporting portions 325 of the substrate. The release sheet is attached to the substrate 340 with a removable/repositionable adhesive.

For this described exemplary embodiment the flexible electrode 348 array is sandwiched between the cover sheet and the release sheet 350. This configuration helps protect the flexible electrode array during shipment. When a clinician applies the flexible electrode array to a patient, the cover is first removed; however, the release sheet is left on the flexible electrode array. As the clinician aligns the flexible electrode array 348 on the patient's back, the release sheet 350 prevents the electrode supporting portions 325 from moving relative to the substrate 340. Once the flexible electrode array is positioned correctly on the patient, the release sheet is removed.

In addition to applications for diagnosing back muscle problems, This described exemplary embodiment of the flexible electrode array can also be used in other types of diagnostic applications such as around body joints, the neck, a hand or foot, or any other area of the body that is operative to bend or flex or is curved. In such cases the pattern and sizes of electrodes can be printed on the flexible supporting sheet to suit the particular application. For instance, when diagnosing problems with a hand such a carpel tunnel, the supporting sheet could be cut in the shape of a hand. Individual electrodes may then be printed along portions of the supporting sheet to correspond with fingers, the back of the hand, and the wrist. For other body parts, other shapes and patterns of electrodes can be used.

The exemplary embodiment of the flexible array as shown in FIG. 43, includes a pair of connection ends 296 and 298. Each of the electrical trace lines terminates at one of these connection ends. To aid in the coupling of the trace lines to an external electrical connector, the trace line ends in connection points 299 which have an exposed electrically conductive surface and have a size that is operative to mate with electrical contacts of an electrical connector.

To help protect the exposed connection points 299 from damage during shipment and storage and from accidental contact with a ground or voltage source, the connection ends 296 and 298 include tail flaps 360 and 362. As shown with reference to tail flap 362, only an end portion 366 of the tail flap 362 is attached to the connection end 298. The tail flap 362 is comprised of a flexible material that enables the portions of the tail flap 362 above the connection points to be lifted away from connection points 299. In this described embodiment the tail flap 362 includes tabs 370, and 372 which assist in lifting the tail flap by hand or by an electrical connector when the connection end is inserted into an electrical connector.

Figure 48:
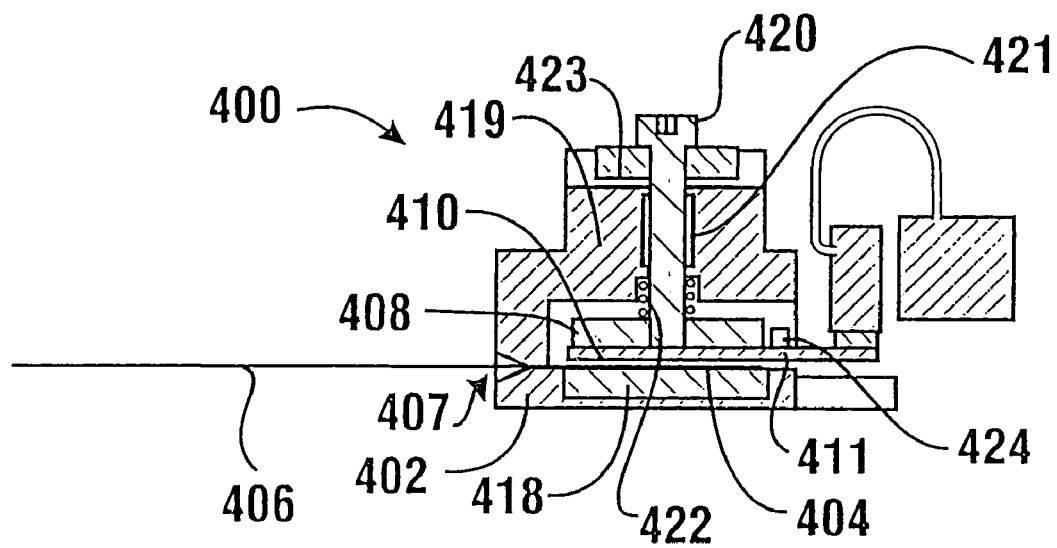
FIG. 48 is representative of a cross sectional side view of a electrode array connector.
Figure 49:
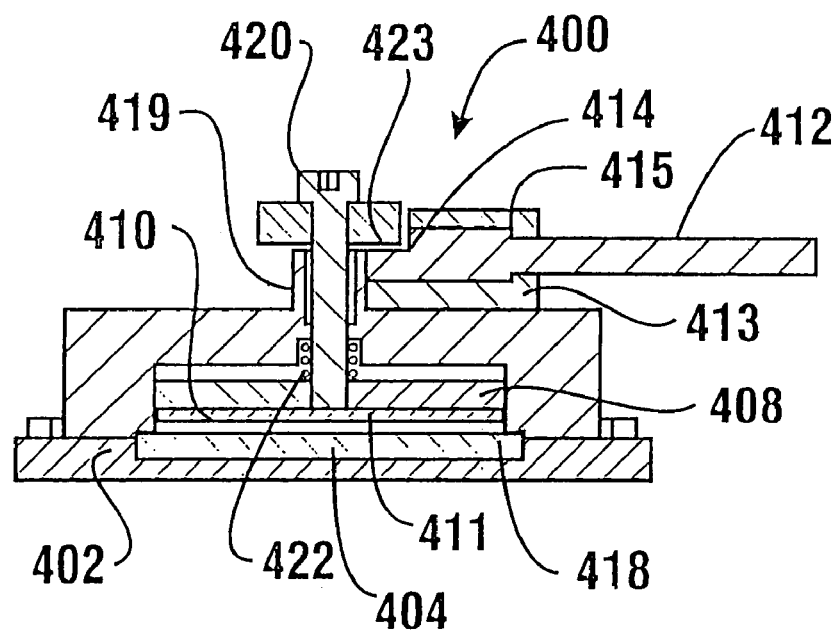
FIG. 49 is representative of a cross sectional front view of the electrode array connector.
Figure 50:
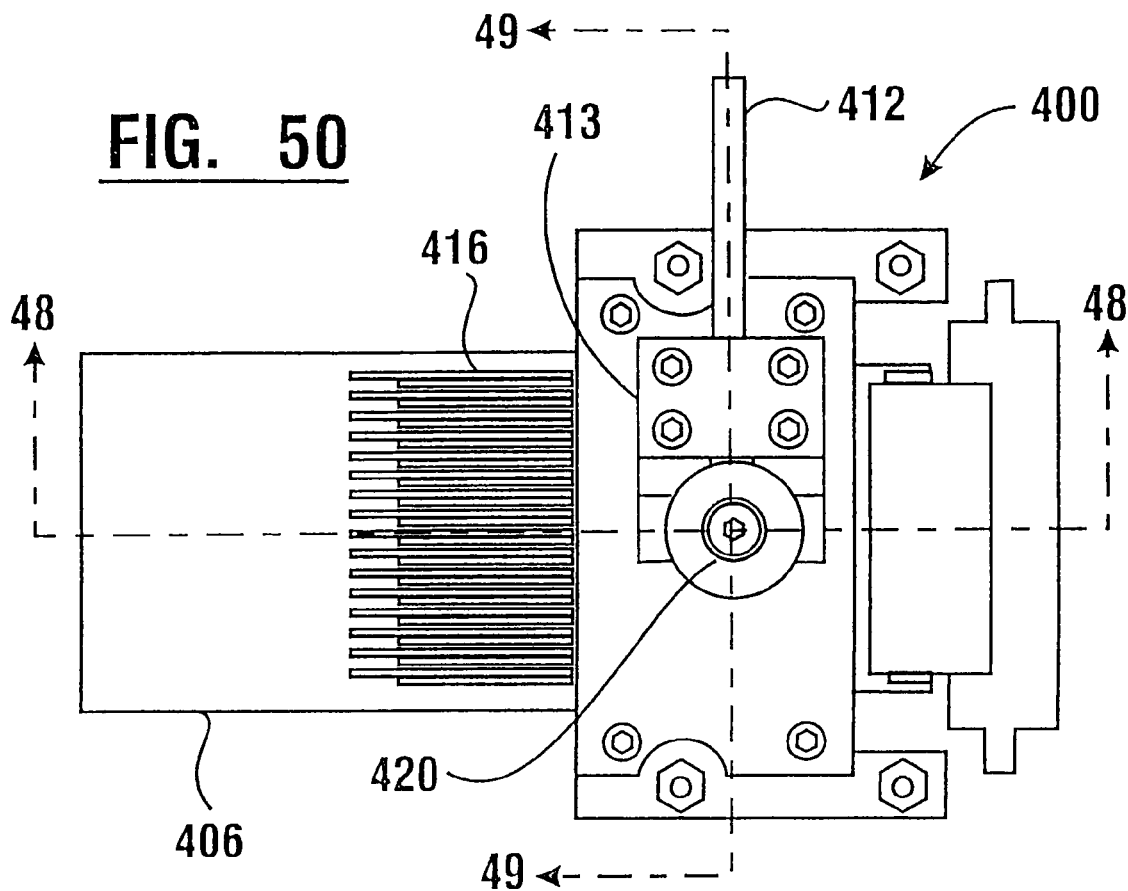
FIG. 50 is representative of a top plan view of the electrode array connector.

An exemplary embodiment of an electrical connector 400 is schematically shown in FIGS. 48–50. This exemplary connector 400 was specifically designed to mate with the connection ends of the flexible electrode array. The connector 400 is a ZIF connector so that wear is minimized between the connector 400 and the connection ends of the flexible array. This extends the usable life of both the connector and the flexible array, thus enabling many mate-demate cycles.

FIG. 48 shows a side plane view of the connector 400 which includes a base member 402. The base member includes a first surface 404 that accepts the connection end 406 of the flexible array adjacent to the first surface 404. The connector 400 also includes a head member 408 that is operative to move with respect to the base member 402. The head member 408 includes a second surface 410 that faces the first surface 404 of the base member 402.

The head member 408 is operative to move between a closed position and an open position. In the closed position the head member 408 is operative to clamp the connection end 406 between the first and second surfaces 404 and 410. When the head member 408 is in the open position, a throat area 407 is formed between the first and second surfaces 404 and 410 with sufficient space to enable the connection end 406 to freely move in and out of the throat area 407.

The connector further includes head guide 419 with a head bore 421 therethrough. The head member 408 includes a follower member 420 that extends in a direction opposite of the second surface 410 and through the bore 421. The follower member 420 is operative to slide back and forth within the head bore.

In the exemplary embodiment, the head member is biased toward the closed position with a spring 422 located between the head guide 419 and the head member 408. However, in alternative embodiments the head member may be biased in the open position.

As shown in FIG. 49, the connecter further includes a shaft guide 413 with a shaft bore 415 therethrough. The shaft bore is sized to accept a shaft member 412 therethrough. The shaft member 412 is operative to rotate within the shaft bore 415. The shaft member includes a cam surface 414 that is in slidable contact with a cam follower surface 423 of the follower member 420. As the shaft member turns, the cam surface 414 is operative to urge the follower member 420 to move within the head bore 419, which in turn moves the head member 408 away from or toward the base member 402.

Figure 51:
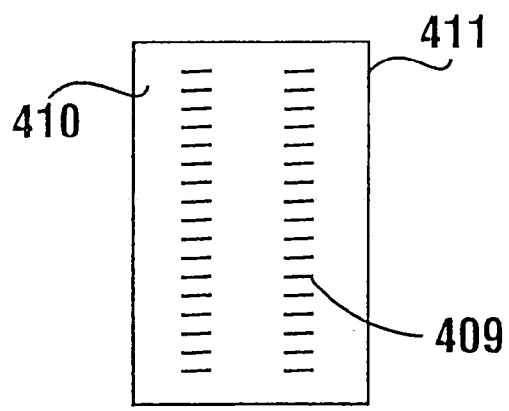
FIG. 51 is representative of a bottom plan view of a head member of the electrode array connector.

As shown in FIG. 50, the connection end 406 of the flexible array includes a plurality of traces 416. As shown in FIGS. 48 and 49, the second surface 410 of the head member 408 includes a printed circuit board 411 with a plurality of electrical contacts 409. As shown in FIG. 51, these electrical contacts 409 are arranged in a predetermined pattern that corresponds to the location of the ends of the traces 416. When the connector end 406 is clamped between the first and second surfaces 404 and 410, each electrical contact 409 on the printed circuit board 411 is in electrical connection with a corresponding trace 416.

Although the exemplary embodiment has electrical contacts located on the head member 408, the present invention encompasses alternative embodiments where the electrical contacts 409 are located on the base member 402 or located on both the head and base members 402 and 408.

In the exemplary embodiment of the connector the first surface 404 of the base member 402 includes a layer of foam 418. When the connection end 406 is locked between the head and base members 402 and 408, the foam 418 is operative to direct the clamping force of the connector evenly across the back of the connection end to achieve good electrical connections between each of the electrical contacts 409 and the traces 416.

To further aid the alignment of the traces 416 with the electrical contacts 409, the connector includes one or more guide pins 424 as shown in FIG. 48. This guide pins 424 are positioned on the base member 402 and are operative to guide the edges of the connection end 406 to positions that will achieve the proper registration between the traces 416 and electrical contacts 409.

Figure 52:
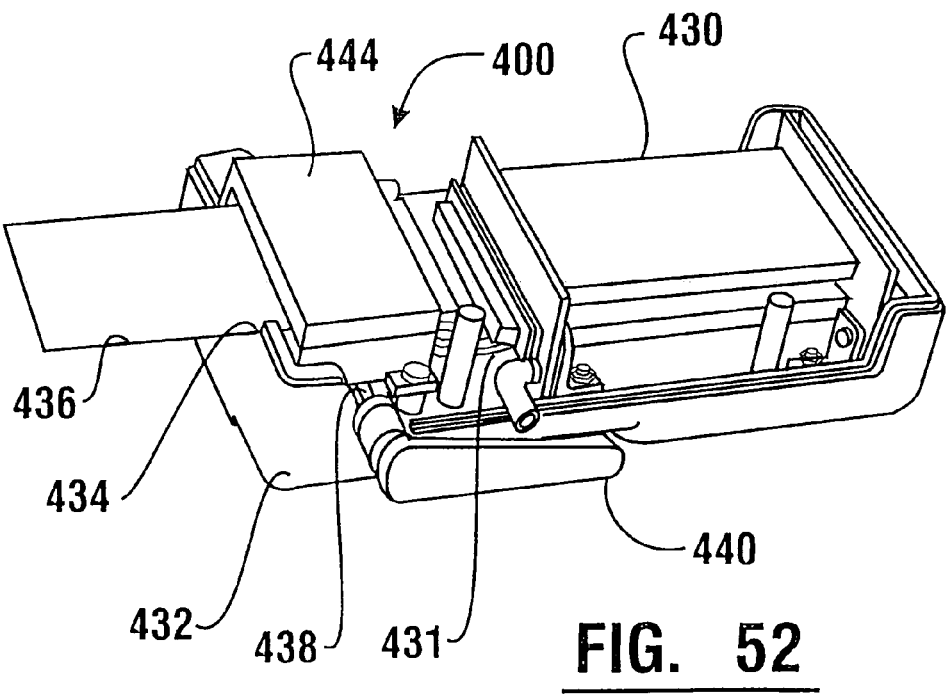
FIG. 52 is representative of an isometric view of a buffer/amplifier coupled to the electrode array connector.

As shown in FIG. 52 a buffer/amplifier 430 is connected to one of the described exemplary connectors 400 to enable the electrical coupling of a flexible array connection end 436 to the buffer/amplifier 430.

For the exemplary embodiment, both the buffer/amplifier 430 and the connector 400 are located in a common housing 432. Each of the electrical contacts in the connector are in electrical connection with the buffer/amplifier 430 through a cable 431. The housing includes a slot 434 that enables the connection end 436 of a flexible electrode array to pass through the housing and slide adjacent the base member 444 of the connector 400.

Figure 53:
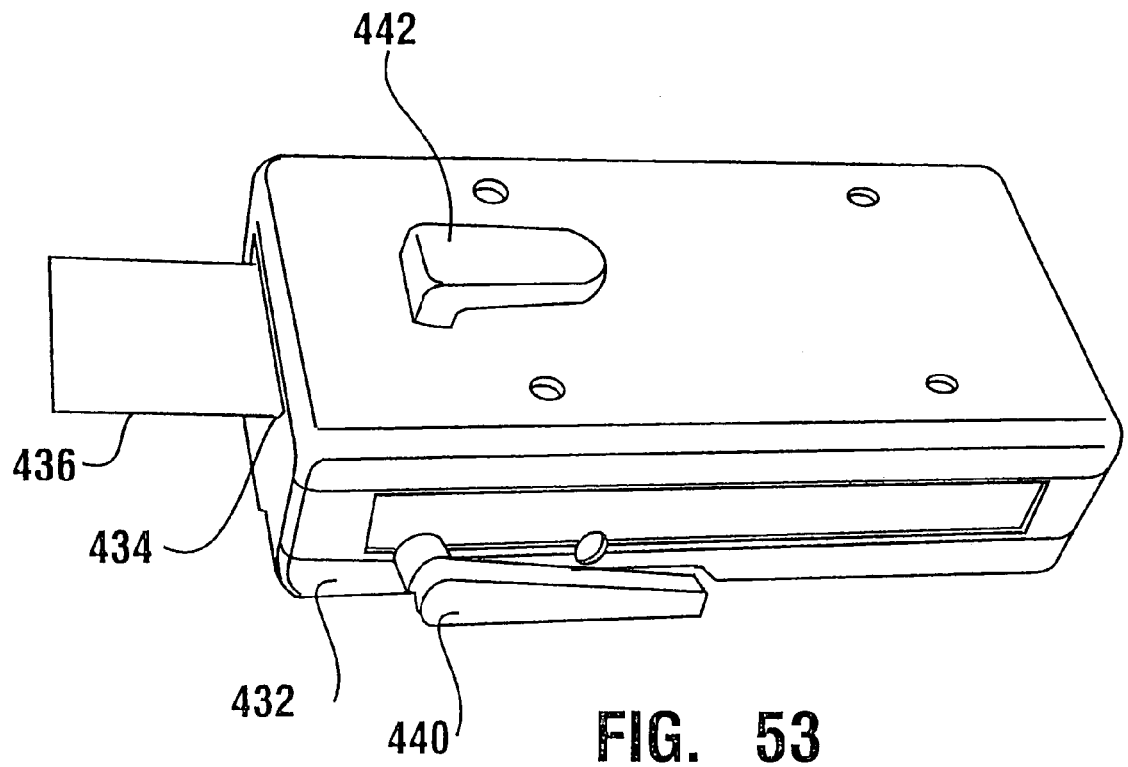
FIG. 53 is representative of an isometric view of a housing enclosing the buffer/amplifier coupled to the electrode array connector.

In this described embodiment the shaft member 438 of the connector includes a lever 440 that extends outside of the housing. The lever 440 is operative to rotate the shaft member 438 backward and forward, which in turn moves the head member between the open and closed positions. As shown in FIG. 53 the housing 430 may include a clip 442 that enables the buffer/amplifier 430 to easily attach to a belt around the torso or hips of a patient. This allows the buffer/amplifier 430 to be easily positioned as close as possible to the origin of the EMG signals being collected from the patient.

The system will now be further described with reference to use of the sensor pad 10 and electrode 28. It should be understood that except as otherwise specified other sensor electrodes, electrode arrays, and supporting structures may be used in a comparable manner to that discussed herein.

Once sensor pad 10 has been located in position on a patient 48 and secured by support belt 49 and electrical interconnection made with electronic apparatus 22, the patient can be moved about and put through a series of different positions in order to develop a series of signal groups indicative of the underlying musculature. Typically, these positions are neutral, flexion, extension, left flexion, right flexion, left rotation, right rotation, sit, supine and prone, although various modifiers or alternatives may be added to or deleted from these positions. In each of the positions a scan of the electrodes 28 is made, each scan requiring only 1–10 seconds, and the signal information retained for later utilization in electronic apparatus 22.

Electrical signals from electrodes 28 are connected by way of wires 40, buffer amplifier 42, filters 43, 44 and cable 45 to analog to digital (A/D) converter 24 and then to computer 25 for analysis and conversion. The data from sensor pad 10 is collected in pseudo differential fashion, each electrode 28 being sampled relative to reference electrode 61 located in the center of pad 10. Subtraction of electrical data yields the wave form between the two electrodes of interest and the wave form is subjected to a root mean square (RMS) analysis over a predetermined time interval to yield a discrete number indicative of the signal strength. In one example of utilization of the signals, the RMS number is converted to a representative color indicia and that color indicia is displayed on the screen of display unit 26 in a location representative of the particular two electrodes 28 of interest. This data is preferably scaled or otherwise conformed to correspond to the anatomy of the patient as previously discussed using suitable scaling software in the computer.

Figure 7:
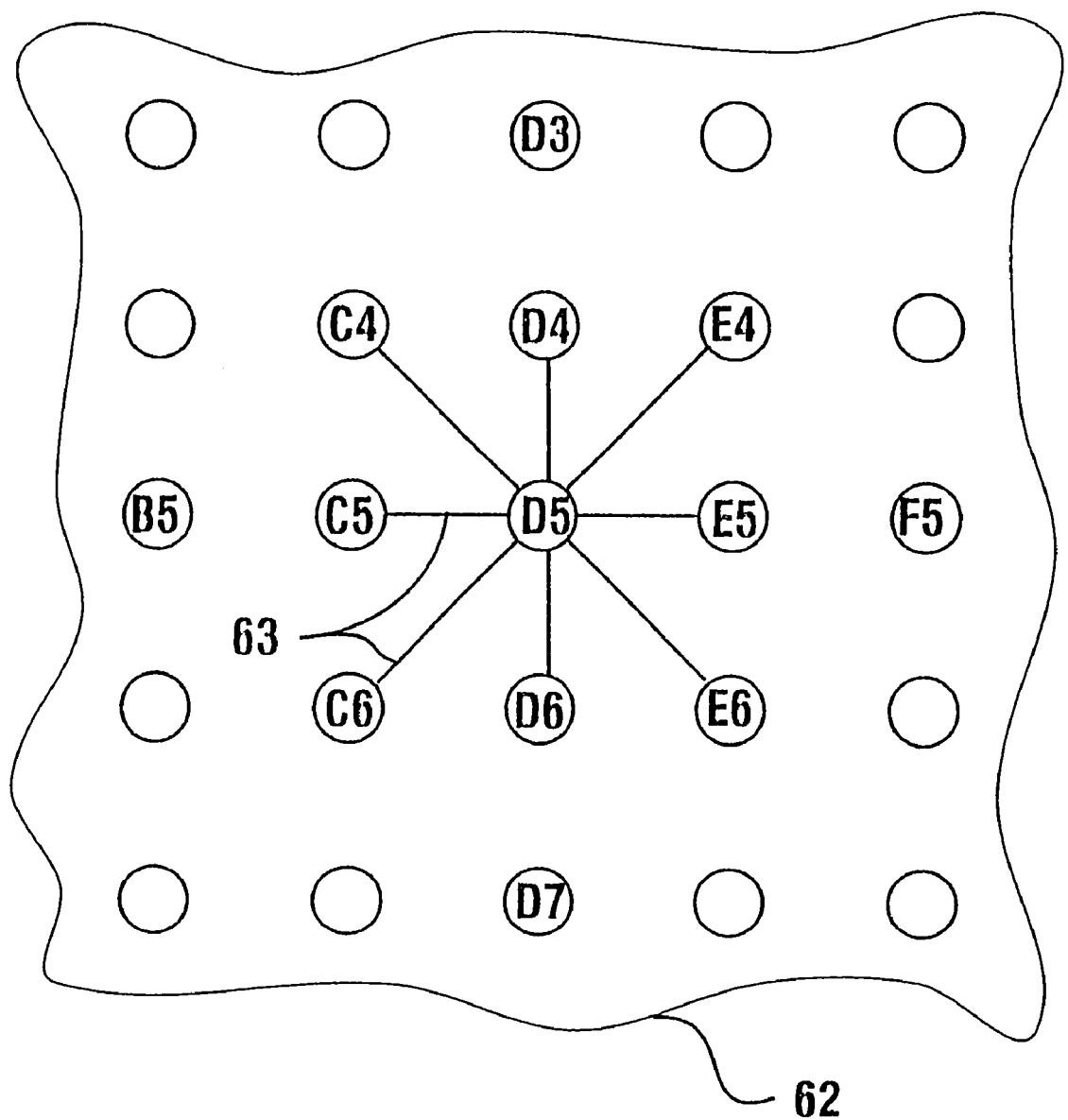
FIG. 7 is a schematic view of the screen of the display unit of the invention depicting the location of a portion of the electrodes of the sensor pad as circles and showing several interconnecting color bars.

This technique of measurement may best be seen in the FIG. 7 representation of a portion of the screen 62 of display unit 26. Here the electrode positions are represented by circles with alphanumeric designations therein, with the seven columns of electrodes 28 designated from A–G and the nine rows designated from 1–9. Thus, various electrode positions are shown, for example, as C4, D5, E6 with D5 representative of the reference electrode 61 position. Intermediate computer generated light bars or line segments 63 interconnect various ones of the adjacent electrode positions, i.e., C5–D5 and C6–D5 to represent the pattern of image generated by computer 25 and displayed at screen 62 of display unit 26.

Figure 3:
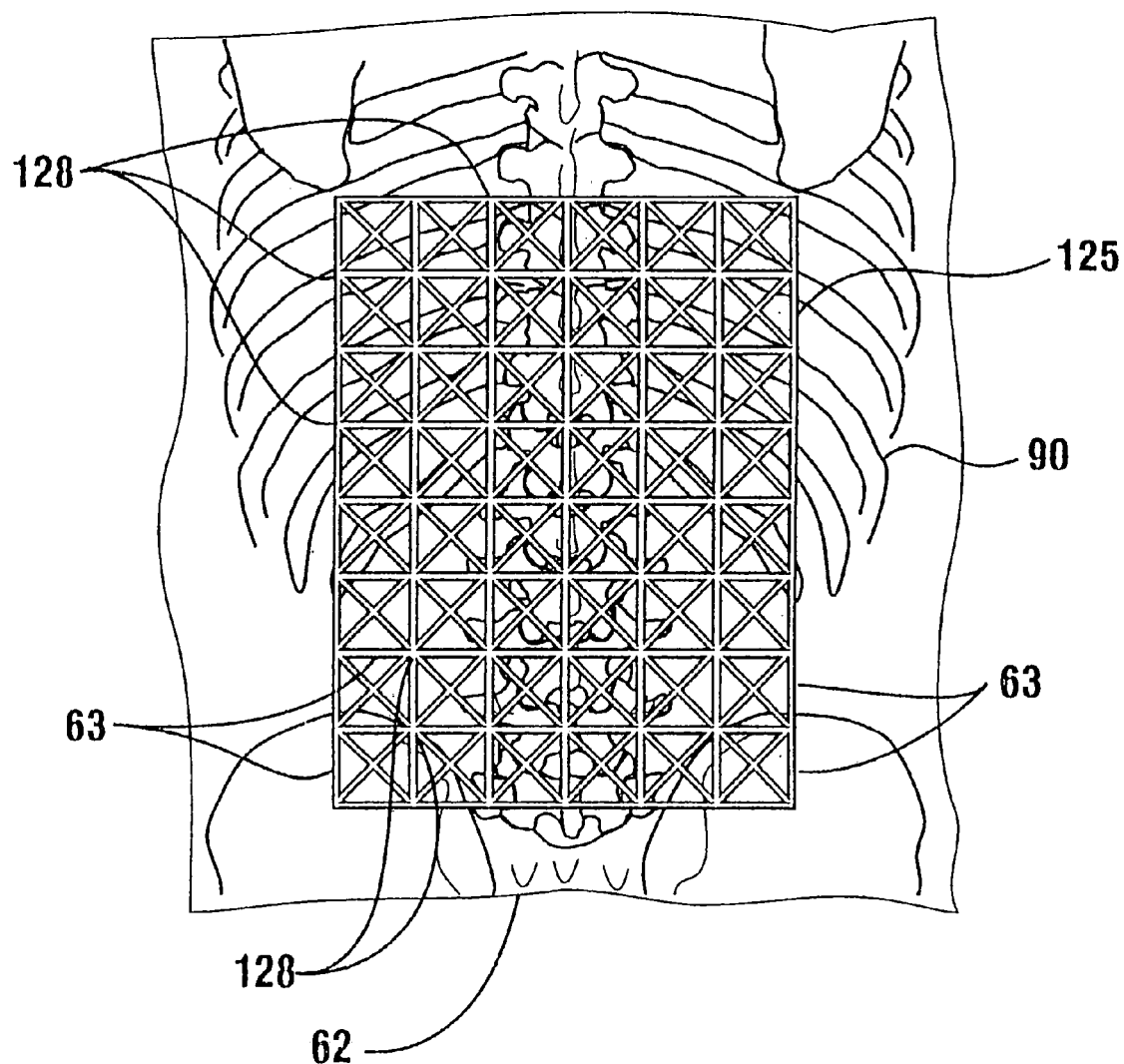
FIG. 3 is a schematic view of the screen of the display unit of the invention showing a full color bar matrix overlay in relation to the lower back skeletal anatomy of a human patient.

A full pattern display is shown in FIG. 3 wherein the screen 62 of display unit 26 shows the full array of light bars 63 interconnecting all of the electrode 28 positions, in a matrix overlying a display of the lower back skeletal anatomy 90 of the patient 48. This view demonstrates the spatial relationship among the locations of electrodes 28, the visual display of light bars 63 and the patient 48 anatomy 90 in a manner that can be readily visualized and utilized by the examining physician. It will be described in greater detail hereinafter that the light bar 63 display can be adjusted or modified by the physician, or automatically by the computer to produce effects including a more limited visual display of light bars 63, or variations in intensity, hue or colorization thereof to enhance the desired display. Further, it will be shown that instead of the skeletal structure 90 of the patient 48, various depictions of the standard musculature of the patient such as those templates shown in FIGS. 15–23 can be made to induce a correlation between the signals being obtained from the sensing electrodes and the specific musculature creating the abnormal condition affecting the patient.

In a scan of the complete array of electrodes 28, 206 color bar images are produced on display unit 26 in positions delimited by and corresponding to the positions of the electrodes 28 on sensor pad 10. Also superimposed on display unit 26 is a graphical depiction of the musculature of the lower back of patient 48 with correlation between the two being achieved by the registration process previously described where a sensor pad is located relative to the tenth thoracic vertebrae 18 and the PSIS identifying crests 12, 14 or the L4 vertebrae, and using appropriate scaling.

In a exemplary embodiment of the invention the diagrams of the musculature of FIGS. 15–23, may be shown at the screen of display unit 26 as a series of images, each representative of certain muscle groups of the lower back of patient 48 so that the attending physician might make a correlation between the colors which represent the strength of contraction of the muscle underneath the electrode and the particular muscles or muscle groups, and discern what muscle is causing the particular colonization patterns being produced. It is apparent as well, that it would be possible to program computer 25 to recognize abnormal signals from the electrodes 28 being polled to provide some other indication of the abnormal situation using different evaluation techniques. It is also apparent that the signals collected from electrodes 28 can be stored in a database and processed in different ways, perhaps at later times or printed out in hard copy, if this is a desired result. The capture of data from all of the electrodes 28 occurs substantially simultaneously and is stored in computer 25 for manipulation in a myriad of possible ways, only certain of which are described herein.

Figures 10, 11:
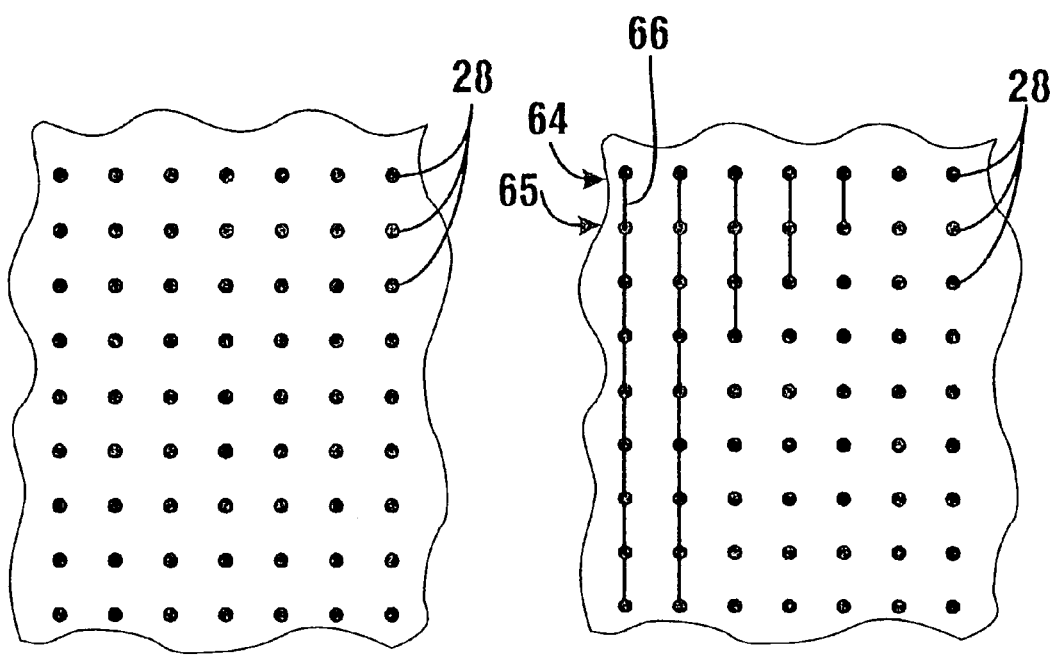
FIGS. 10–13 are schematic views of the screen of the display unit showing various configurations of color bar displays.

Referring now to FIGS. 10–13, there are shown several variations of the techniques for monitoring and analysis of the electrical signals derived from electrode 28. As previously described, each electrode 28 is scanned relative to reference electrode 61 to develop a signal representative of the voltage level detected at the site of the particular electrode, and data representative of the signal retained in computer 25. In further processing of the signals, each signal may be compared to that of other electrodes to develop signal patterns representative of the muscle condition being evaluated. For example, FIG. 10 is a representation of signals developed at sensor pad 10 when only a depiction of a discrete color dot is made at the location of each electrode 28, with no showing of color bars. This display might be most useful in achieving a desired registration between electrode 28 display and the skeletal structure 90 display.

FIG. 11 describes a first variation for analysis of the signals where the signal of each electrode 28 in the first row 64 is compared to the corresponding electrode 28 in the same column, in the second row 65 to develop a resultant signal, represented at display unit 26 as a bar 66 joining the location of the particular electrodes. In this manner a full pattern of vertical bars 66 is developed, although only a portion is shown, with each being a unique color and representative of the signal comparison at each electrode pair. Such arrangement of color bars 66 may be displayed juxtaposed to patterns of muscle structure as previously described, and likely is more useful in displaying an association with muscles or muscle groups which are oriented generally vertically in the back of the patient.

Figures 12, 13:
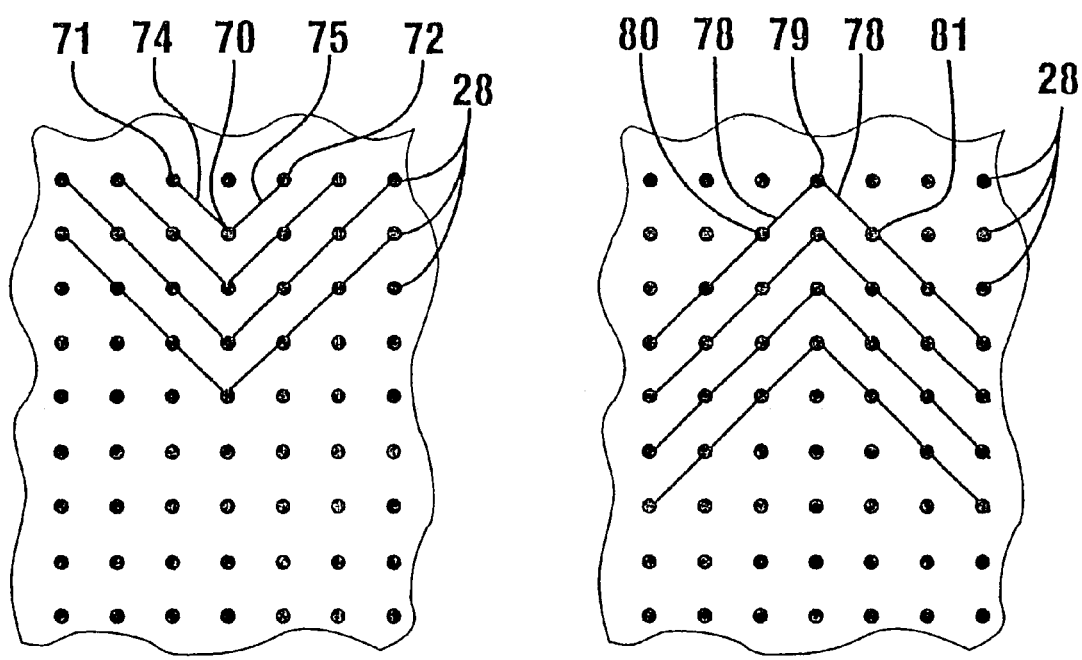
Figure 14:
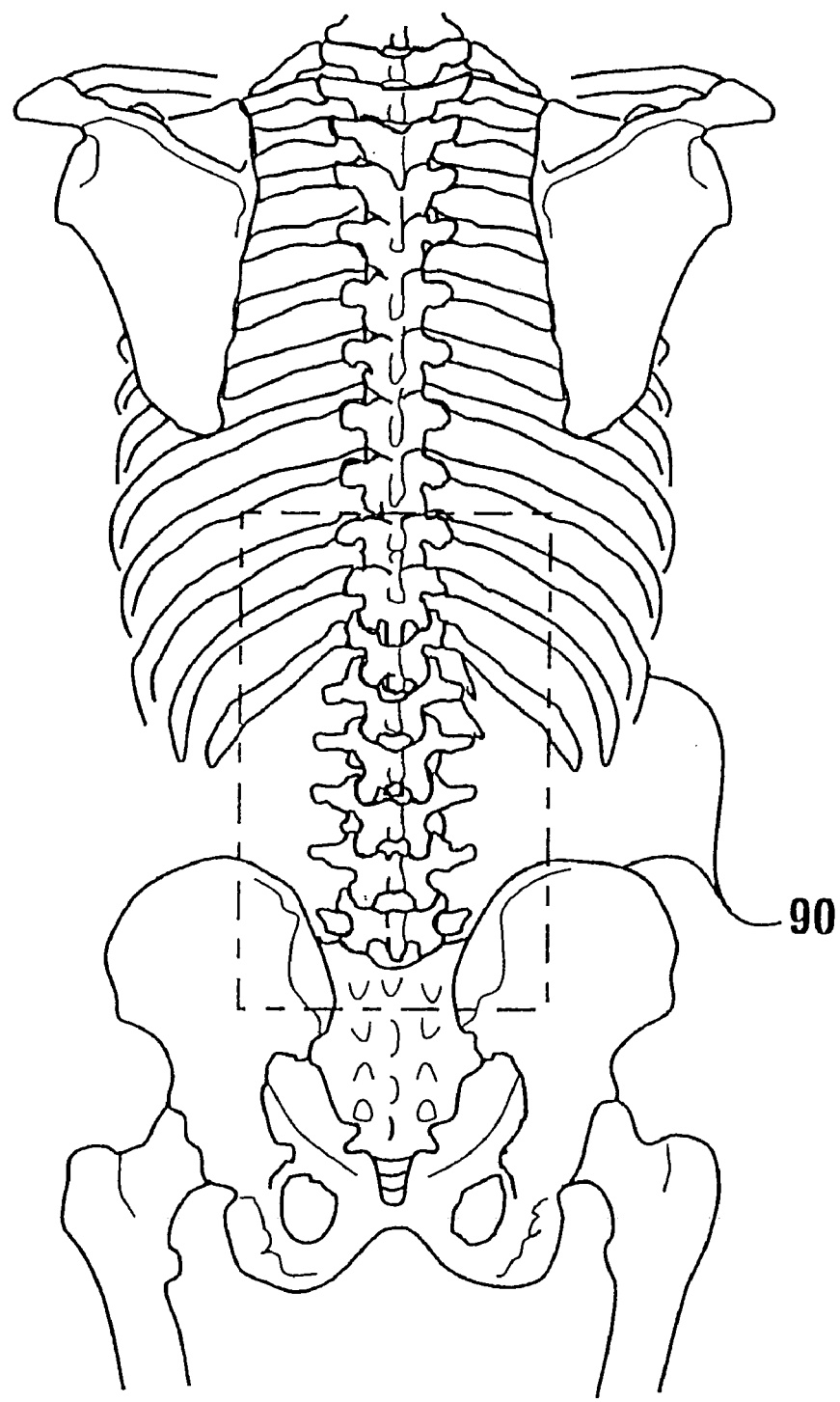
FIG. 14 is a schematic diagram of skeletal anatomy associated with the lower back of a normal human patient.
Figure 15:
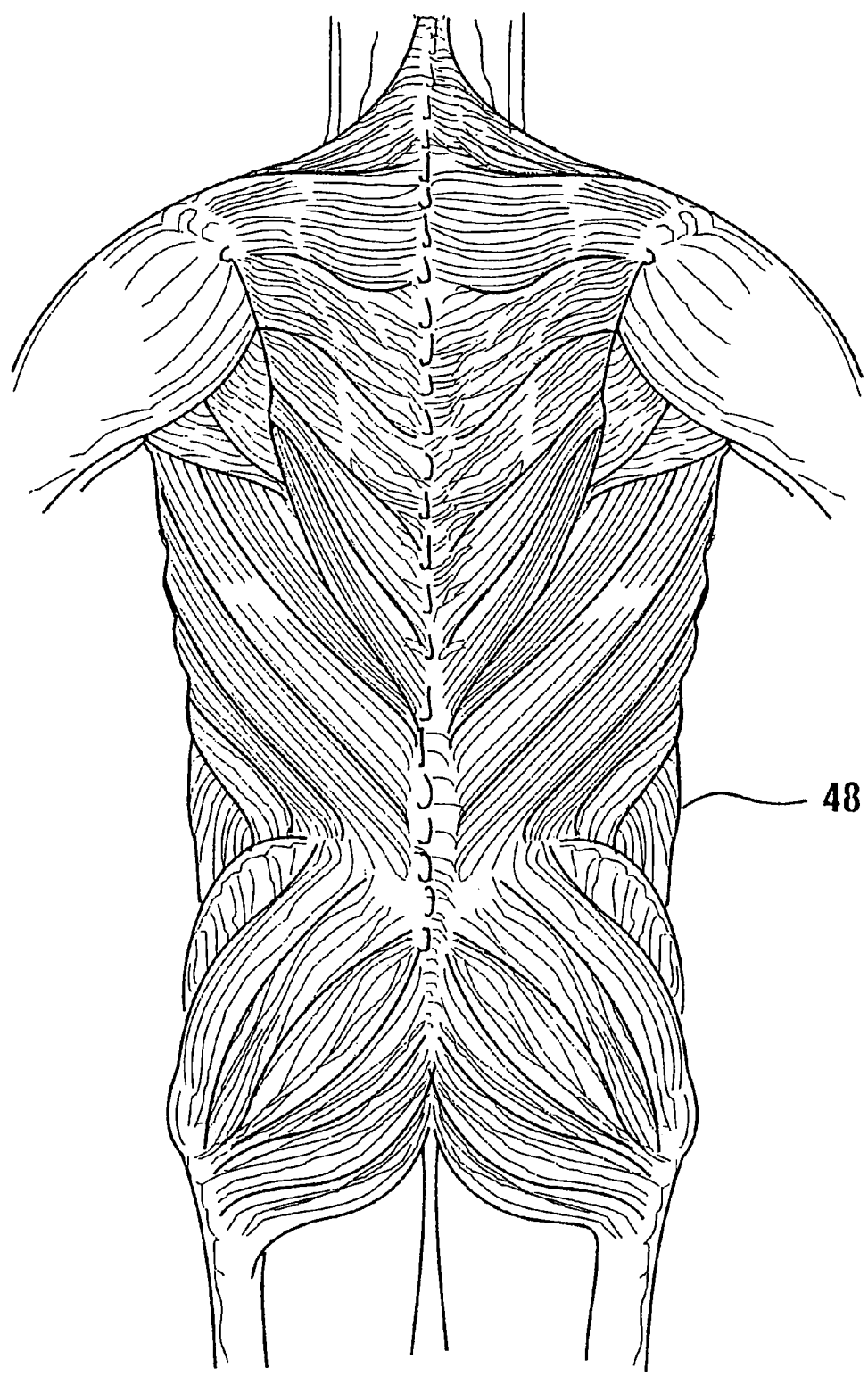
FIGS. 15–23 are schematic diagrams of various groups of musculature of a normal human patient shown in relation to the skeletal anatomy of FIG. 14.
Figure 16:
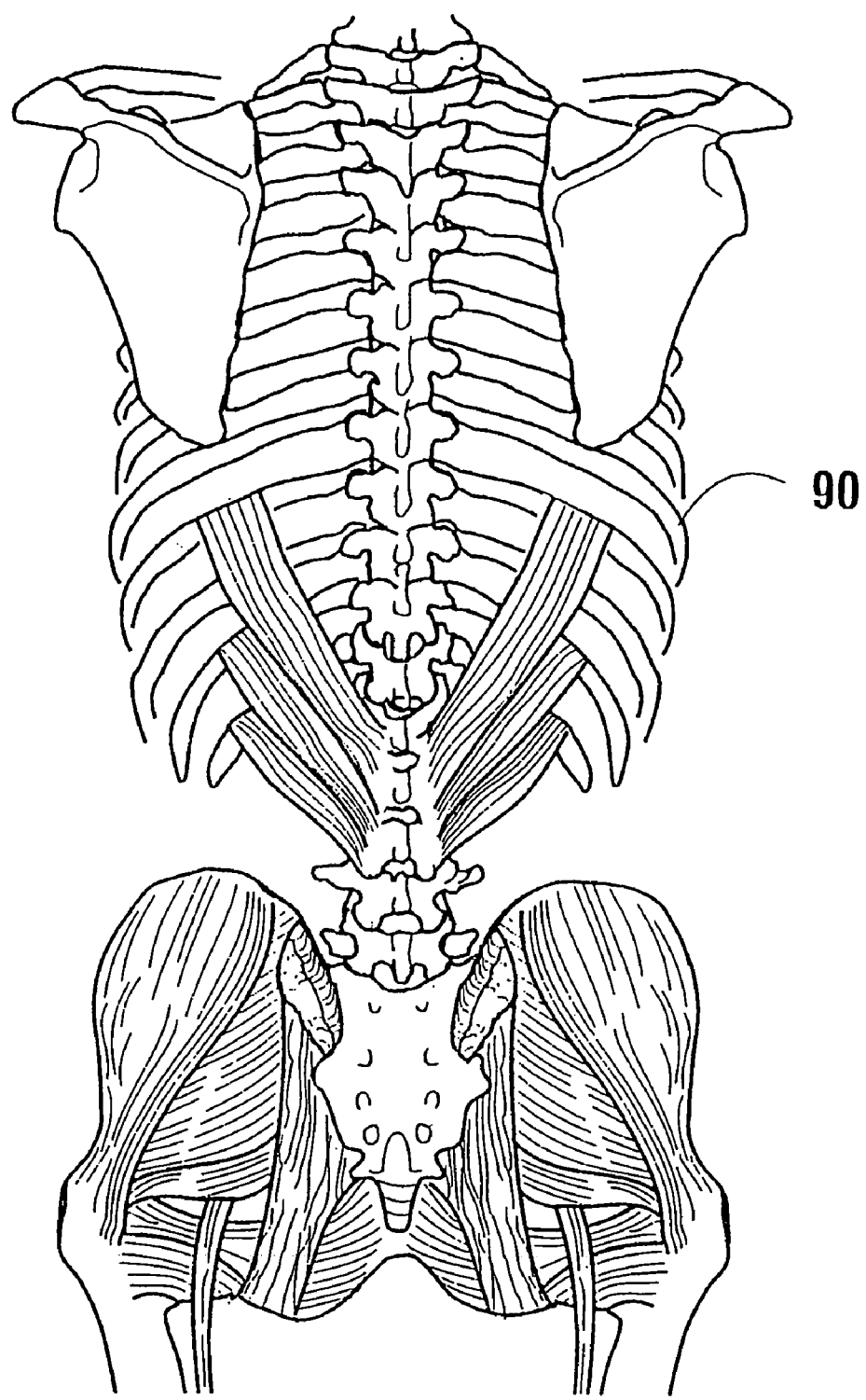
Figure 17:
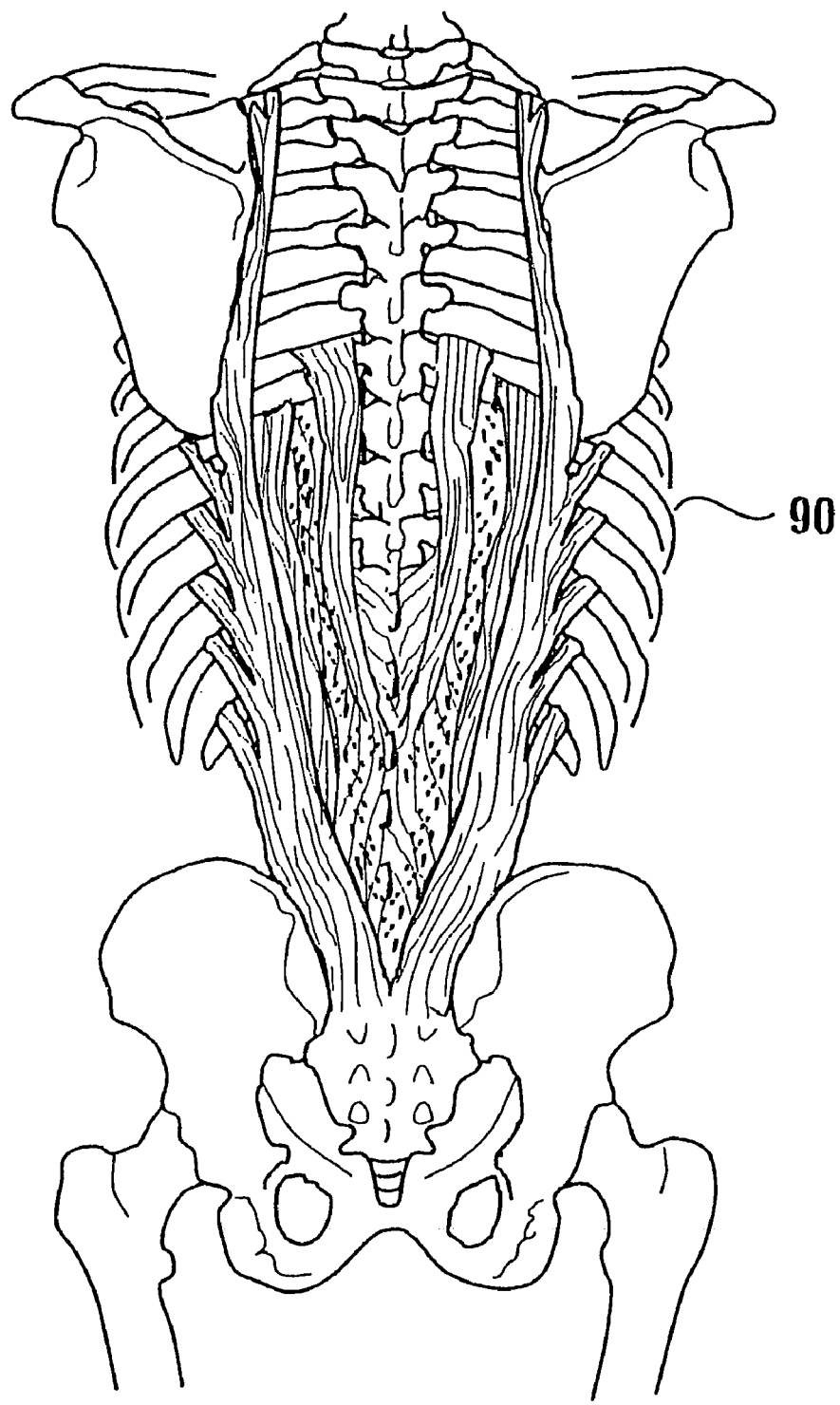
Figure 18:
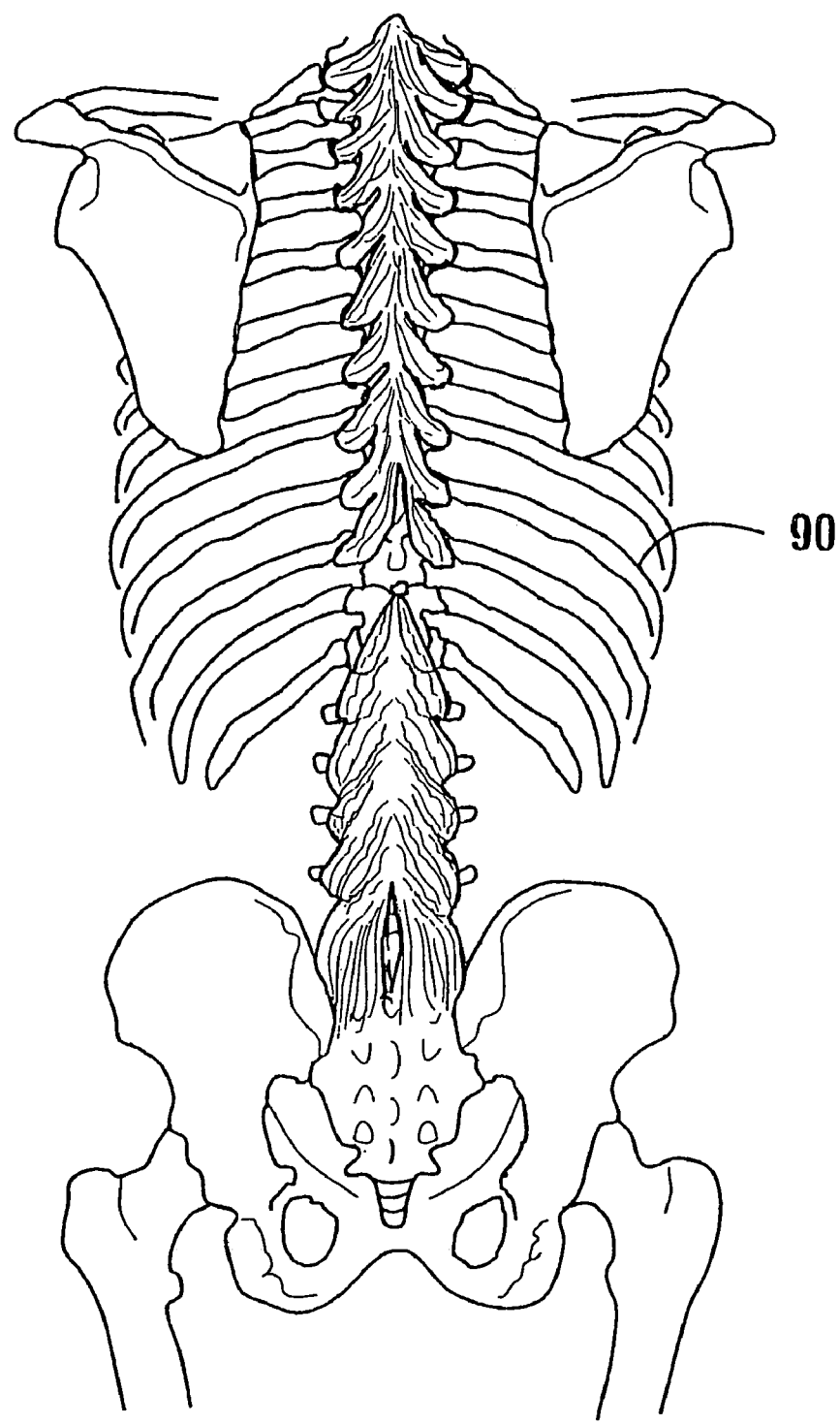
Figure 19:
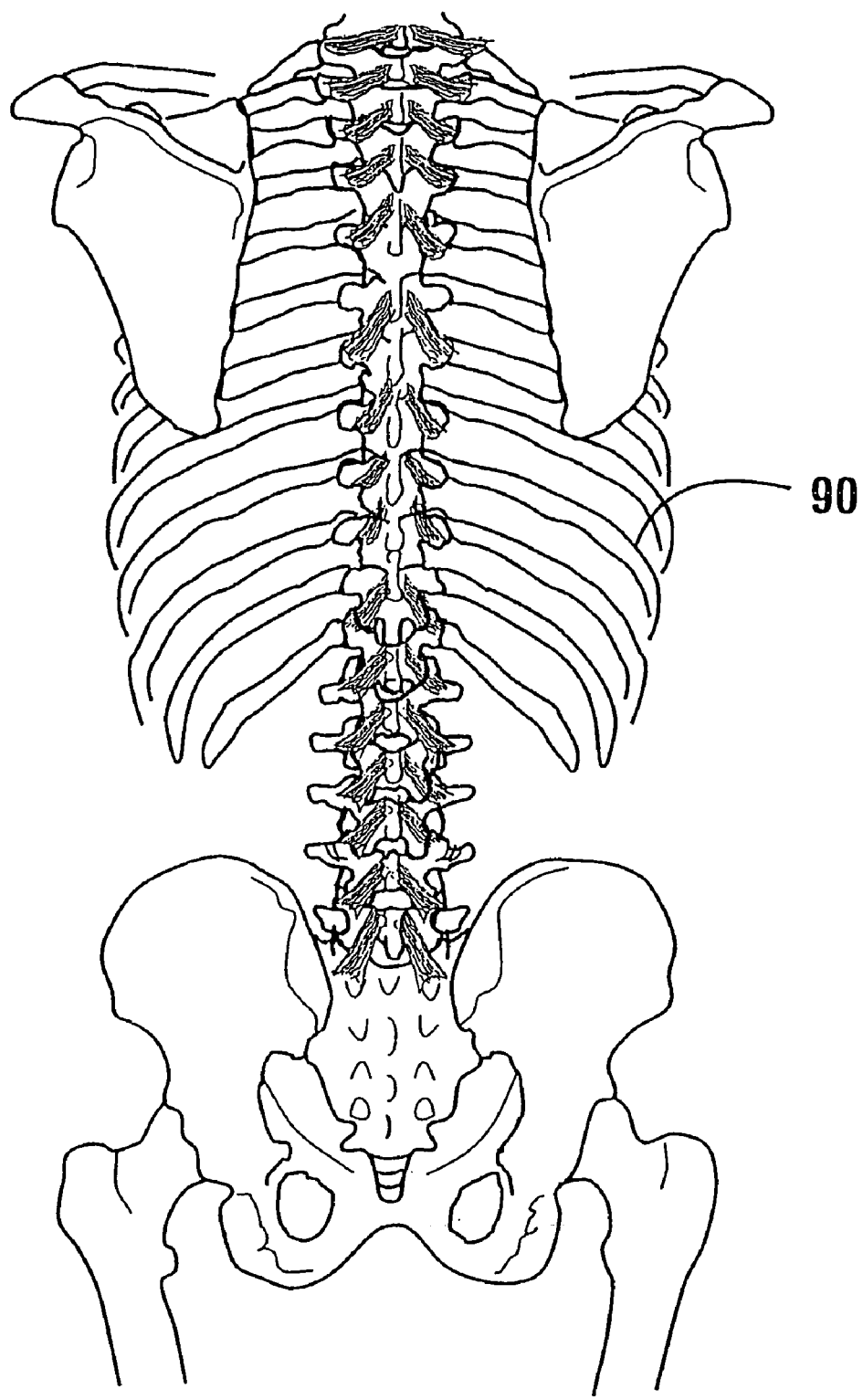
Figure 20:
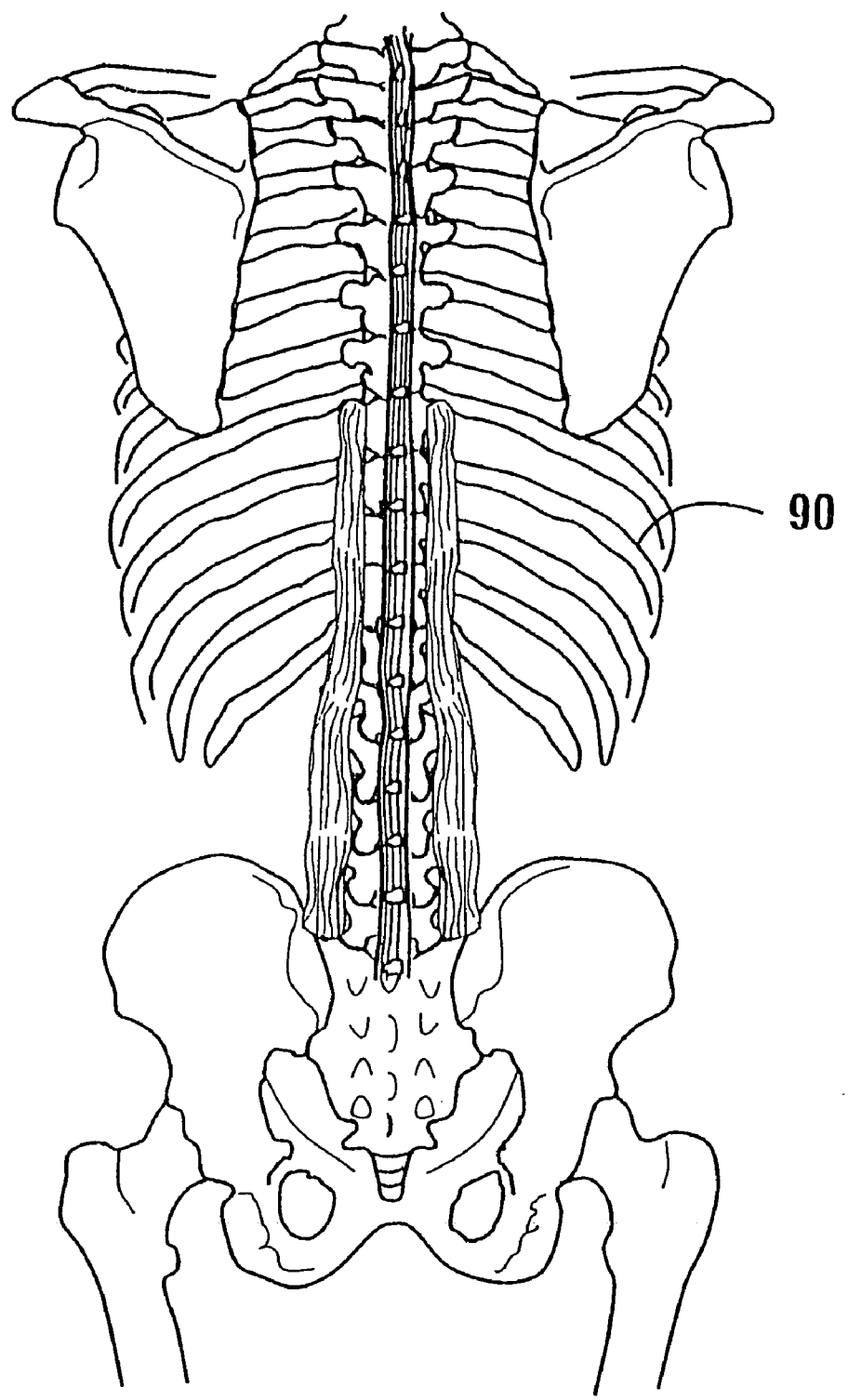
Figure 21:
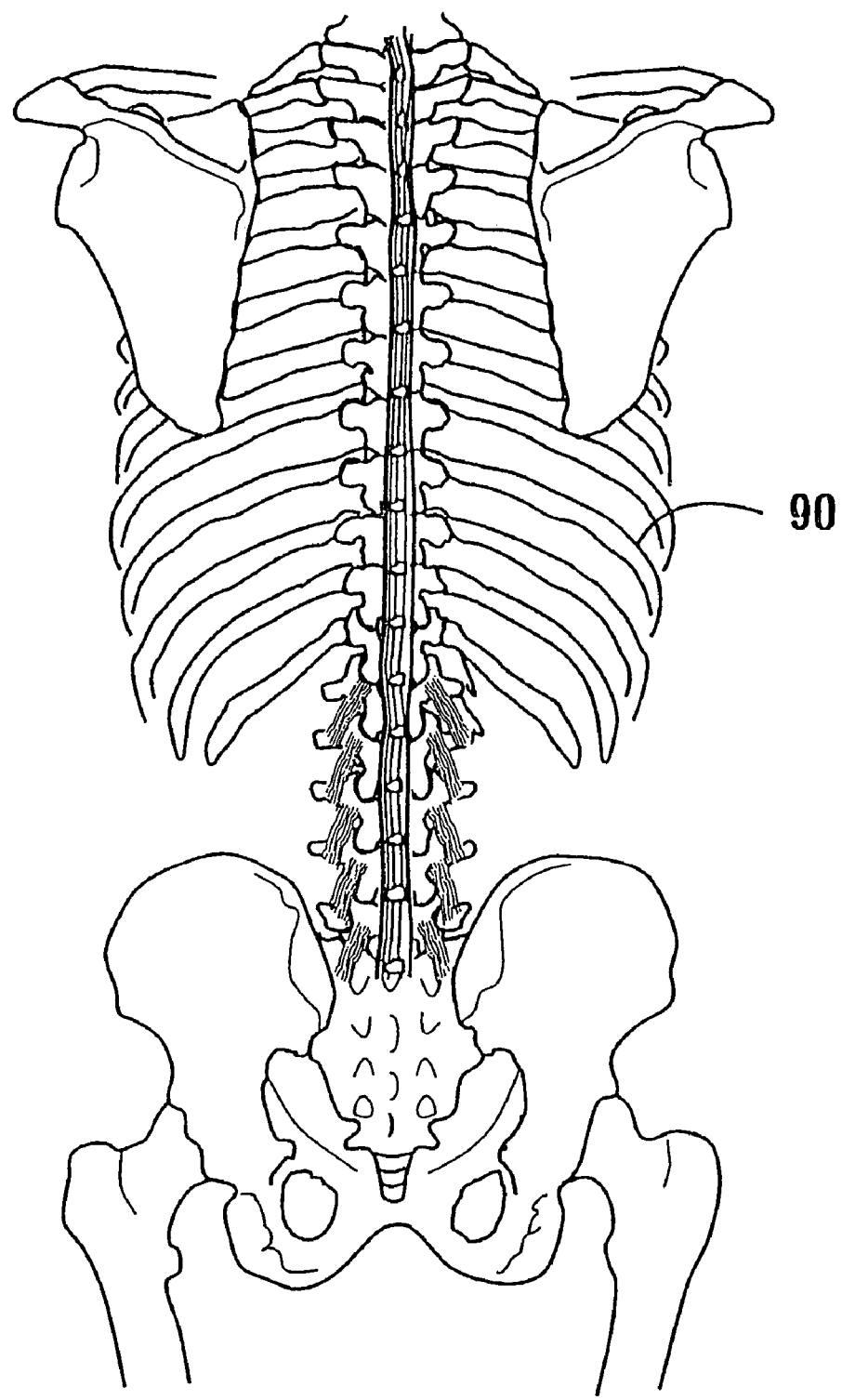
Figure 22:
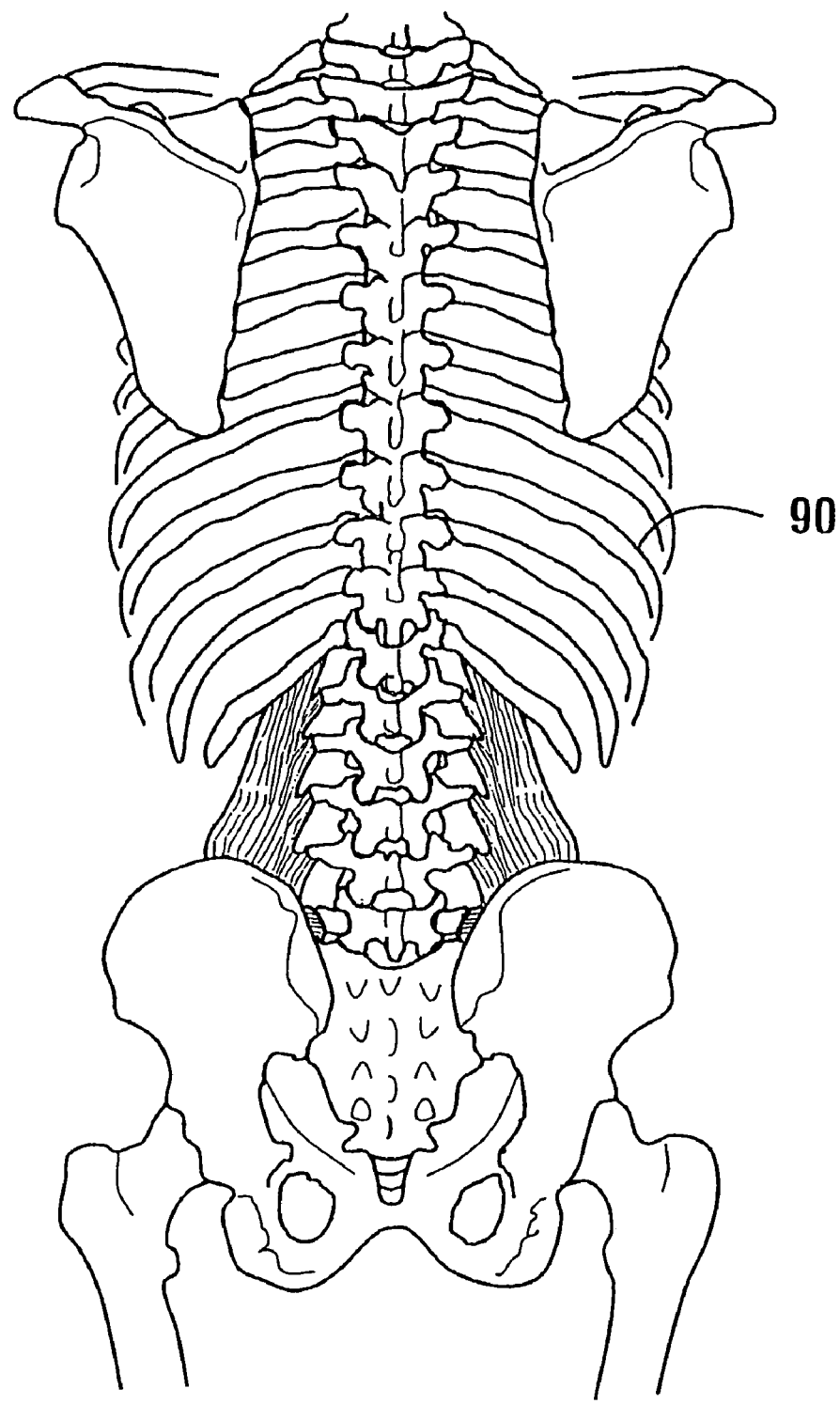
Figure 23:
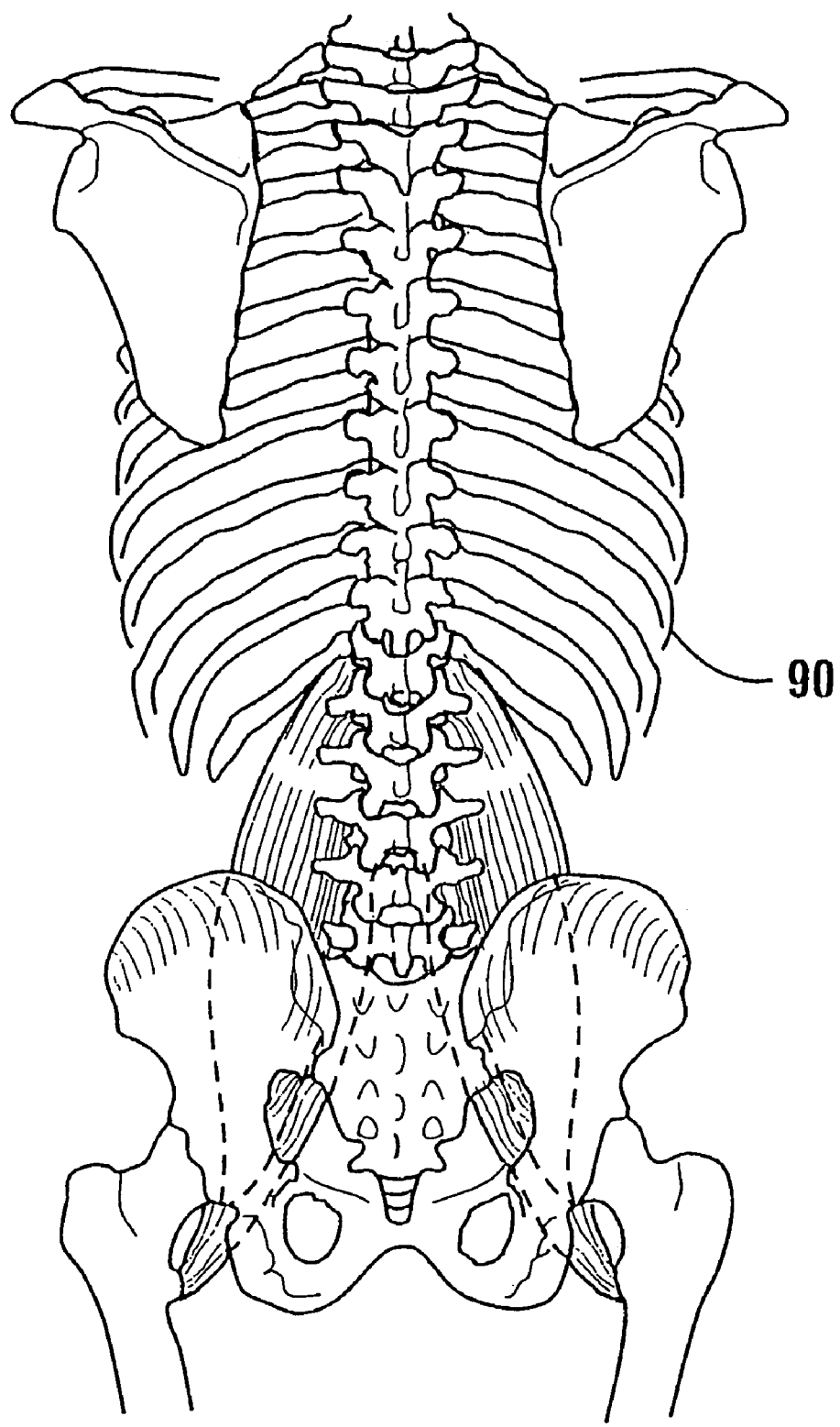

FIGS. 12 and 13 represent yet other variations of signal analysis wherein different herringbone patterns of signal are derived. In FIG. 12, for example, the signal of center electrode 70 in the second row, center column (D2) is compared with electrodes 71, 72 in the first row and adjacent columns (C1) (E1) to develop intermediate color bars 74, 75 respectively, indicative of the comparison of the electrode signals. Further color bars corresponding to bars 74, 75 are developed throughout the array of electrodes 28 to achieve an overall pattern for display at display unit 26. Again, only a portion of the display is depicted in FIG. 12, for purposes of clarity.

FIG. 13 is yet another variation of a display that may be produced using this technique of monitoring. Here an inverted herringbone pattern consisting of color bars 78 is achieved when the signals from electrodes 28 are compared in the described pattern. For example, electrode 79 in the first row, center column (D1) is compared to electrodes 80, 81 in the second row in adjacent columns (C2) (E2) to produce the intermediate color bars 78. When extended throughout the array of sensor pad 10, a colored herringbone pattern of color bars 78 is achieved for comparison with muscle pattern displays shown in association therewith.

It is apparent that still further comparisons can be made of the signals obtained from electrodes 28, for example to compare the signal of each electrode 28 with the signals of all adjacent electrodes 28, and electronically summarize the information obtained and to produce a representative color pattern of the results for visualization at the face of display unit 26.

Similarly, it is apparent that the resultant electrical signals from electrodes 28 and the resultant color information can be shown at display unit 26 in different formats to emphasize the relationship between developed signals and the underlying muscle structure. With a suitably high speed computer 25, the images of differing muscle structures can be shown in association with the color patterns as directed by the physician to provide a correlation between the colorization and the abnormal muscle elements.

It will further be understood that in various embodiments different forms of the display may be used including arrangements of various types of pixels or other types of icons or designators which are indicative of levels of muscle activity. While coloration may be a exemplary indicator in the diagnostic tool for purposes of correlating muscle activity and underlying anatomy, other visual outputs may be provided which do not involve coloration for clinicians who suffer from color blindness. Such outputs may involve varying patterns of a monochrome nature which are indicative of levels of muscle activity. Alternatively embodiments of the invention may include other types of output devices which enable the discrimination of levels of muscle activities. Such output devices may also output indicia representative of the underlying muscle topography. This may include for example output devices usable by the visually impaired such as pin array type output devices in which arrays of pins are movable relative to one another to produce surface contours. Such arrays may be produced with sufficient numbers of pins and pin densities to provide contours indicative of underlying musculature as well as electrical activity. Such devices may be multiplexed between received signals and data representative of underlying musculature to facilitate comparison through touch of muscle contour and areas of muscle activity. Such output devices may be combined with visual and other type devices to facilitate diagnosis of conditions even by clinicians who do not have a visual impairment.

Figure 25:
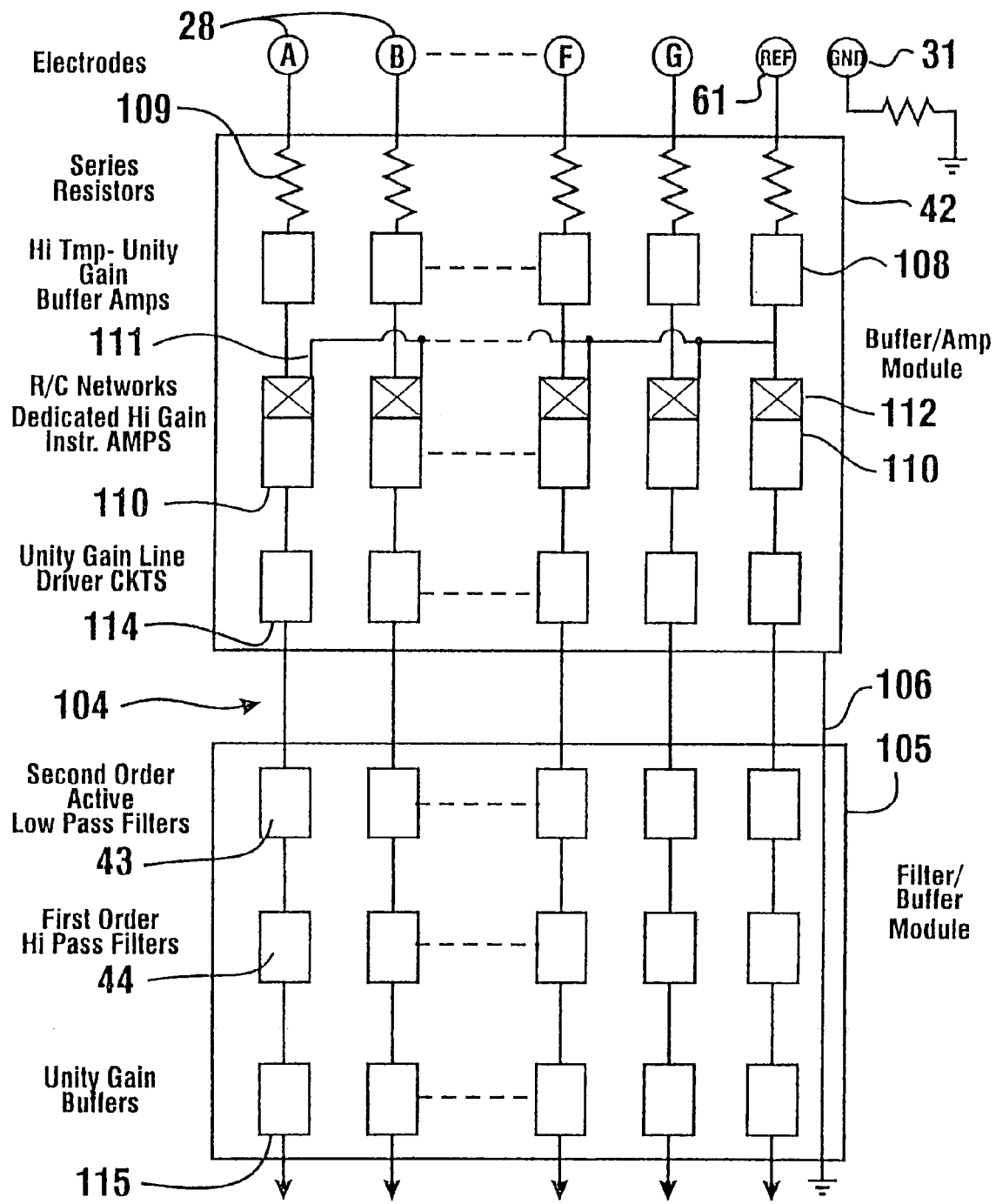
FIG. 25 is a schematic view of the components comprising the Analog Signal Conditioning Subsystem of FIG. 24.

Referring now to FIGS. 24 and 25, there is shown in more detail the components comprising the analog and digital signal portions of one exemplary embodiment of the invention including electrode subsystem 100, analog signal conditioning subsystem 101, and signal processing subsystem 102. Electrode subsystem 100 comprises the array of sixty-three electrodes 28, only a few of which are shown and labeled as A, B, F, G, Ref. and Gnd. in correspondence with previous descriptions. Wires 40 connect electrodes 28 to buffer amplifier 42, shown in block form on FIG. 24 and in more detail in FIG. 25.

A long shielded interconnect cable 104 connects the outputs of buffer amplifier 42 to more remotely located Filter/Buffer module 105 which includes low and high pass filters 43, 44. In turn, a short shield cable 45 completes the analog signal portion, being connected to analog to digital converter card 24 in computer 25, the latter components being essential parts of the signal processing subsystem 102. As indicated, a single continuous shield path, depicted by dashed lines 107, is established between Buffer/Amplifier module 42 and computer 25, assuring that minimal interference is generated in the signals of interest from extraneous sources.

The enclosures used for the Filter/Buffer module 105 and the Buffer/Amplifier module 42 are shielded with a layer of conductive material. All enclosure shields are connected in series with the interconnect cable shields, resulting in a single continuous shield path from the Buffer/Amplifier input connector to the data acquisition computer 25 chassis ground.

The array of electrodes 28 mounted on sensor pad 10, as previously described, must conform to the human back, ensure consistent electrode impedance with the skin, not interfere substantially with patient movement, and be easy to use. The electrodes 28 in this described exemplary embodiment are in a nine row by seven column configuration and the sensor pad 10 is held in place with a fabric brace with or without pressure sensitive adhesive. Of course other configurations of electrodes may be used in other embodiments. Likewise the disposable type and reusable adhesive type sensor arrays discussed previously may be used.

The analog signal conditioning subsystem 101 provides buffering, voltage amplification and analog filtering for the array of electrodes 28. In one embodiment one electrode in the array is designated as the reference electrode 61, and all other electrode voltages are measured with respect to the reference electrode 61. Other embodiments may employ other approaches for acquiring signals indicative of relative levels of electrical activity.

Each of the electrode 28 signals is connected by way of wires 40 to high impedance, unity gain buffer amplifiers 108 by way of a 10K Ohm series resistor 109. The purpose of resistor 109 is to provide a measure of resistive isolation for safety purposes, as well as to increase the electrostatic discharge (ESD) immunity of the amplifier.

Following the buffer amplifiers 108, each channel has a dedicated high gain instrumentation amplifier 110. The inverting input of each instrumentation amplifier 110 is connected to the buffered signal from the reference electrode channel as shown by connector 111. Thus, the output of each instrumentation amplifier 110 represents the voltage of a given electrode with respect to the reference electrode 61. RC networks 112 connected to the inputs of the instrumentation amplifier 110 serve as low pass filters to block unwanted high frequency signals. The outputs of the instrumentation amplifiers 110 feed into unity-gain, line-driver circuits 114 that are capable of driving the capacitive load of the long shielded interconnect cable 104, without oscillation.

The ground electrode 31 is connected to the patient and is connected to ground through a resistor. In one exemplary embodiment electrode 31 is connected to the analog signal ground on the digital converter card through a one million Ohm resistance. The exemplary form of the analog to digital converter card 24, is a sixty-four channel multiplexed converter capable of operating in pseudo-differential input mode. The Buffer/Amplifier module 42 and Filter/Buffer module 105 are each connected to ground as represented by line 106.

Each of the sixty-three signal inputs into Filter/Buffer 105, via cable 104, is connected to a second order active low pass filter 43. The output of low pass filter 43 is connected to the input of first order, high pass filter 44. The output of each high pass filter 44 is connected to unity gain buffer 115 that is capable of driving the capacitive load of the analog to digital converter card 24 interconnect cable 45, without oscillation. Electronic power for Filter/Buffer module 105 is provided by an external linear power supply. Filter/Buffer module 105 provides power for Buffer/Amplifier module 42 via the interconnect cable 104. Ground sense line 106 from the Buffer/Amplifier modules 42 passes directly through the Filter/Buffer module 105.

Figure 26:
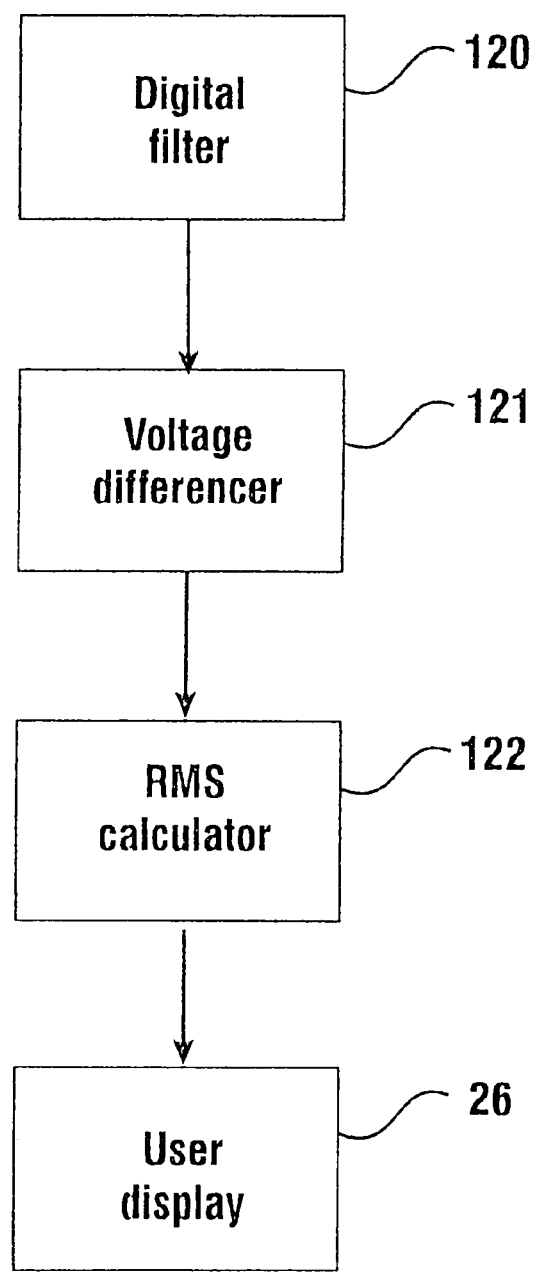
FIG. 26 is a schematic view of the components comprising the Signal Processing Subsystem of FIG. 24.

Signal processing subsystem 102 is shown in block diagram form in FIG. 26 and consists of the major elements of a digital filter 120, voltage differencer 121 and RMS calculator 122. First, digital filtering techniques are used to reduce noise on the measured signal. Next, a voltage differencer 121 determines the voltage waveform between all adjacent electrodes 28. Finally, the root-mean-square (RMS) voltage between all adjacent electrodes is calculated and used to characterize the level of muscle activity between adjacent electrodes. The signal processing subsystem is preferably implemented in software on a PC-compatible computer 25.

The digital signal conditioning system consists of high pass, low pass and band-cut digital filters incorporated into the data analysis software. The high and low pass filters are designed to reject signals outside of the frequency range of interest, and have amplitude rolloffs of 80 dB/decade. The primary purpose of these digital filters is to block common-mode error signals introduced near the corner frequencies of the analog filters. The band-cut or notch filter drastically reduces 60 Hz signals, in order to eliminate unwanted pickup of power line emissions. In one exemplary form of the invention oversampling is used which interpolates additional pseudo sample points between actual sample points to improve performance of filters, for example to achieve good frequency discrimination in the 60 Hz notch filter. In one exemplary embodiment 10X oversampling is used.

The output of the electrode voltage data acquisition subsystem consists of a set of voltage waveforms of each electrode 28 with respect to a particular reference electrode. The voltage differencer 121 computes the voltage waveform between each pair of adjacent electrodes (vertically, horizontally and diagonally) by differencing the voltage waveforms for the two adjacent electrodes. RMS calculator 122 provides the RMS value of each adjacent electrode pair waveform as a scalar number which is computed from the waveform using a conventional RMS calculation.

The user display subsystem 26 presents the processed data to the practitioner in a readily understandable format. In the described embodiment the data is displayed as images on a screen or other visual output device. Of course as discussed previously, in other embodiments other output devices may be used. A digitized illustration of a muscle layer in the human back as shown in FIGS. 14–23 is used as the background of the image. The user may select any muscle layer as the image background. A computer generated image 125 of the processed electrode 28 data is overlaid on the selected background illustration, and is spatially registered to that image. As previously discussed the spacial registration may be preferably achieved through scaling based on the dimensions of the patient input to the computer.

The electrode data image 125 in the described embodiment consists of colored lines or light bars 63 drawn between the locations of each of adjacent electrodes 28, which are at each intersection 128 of each of the seven vertical columns and nine horizontal rows of light bars 63 as shown in FIG. 3 and as has been previously described. The color of each line 63 indicates the value of the RMS voltage between the adjacent electrodes. The user can dynamically specify a maximum RMS value and a minimum RMS value which are used to map voltages to colors. The resulting display is thus a false-color RMS voltage gradient field display, and is overlaid on and registered to the underlying muscle layer illustration.

Figure 27:
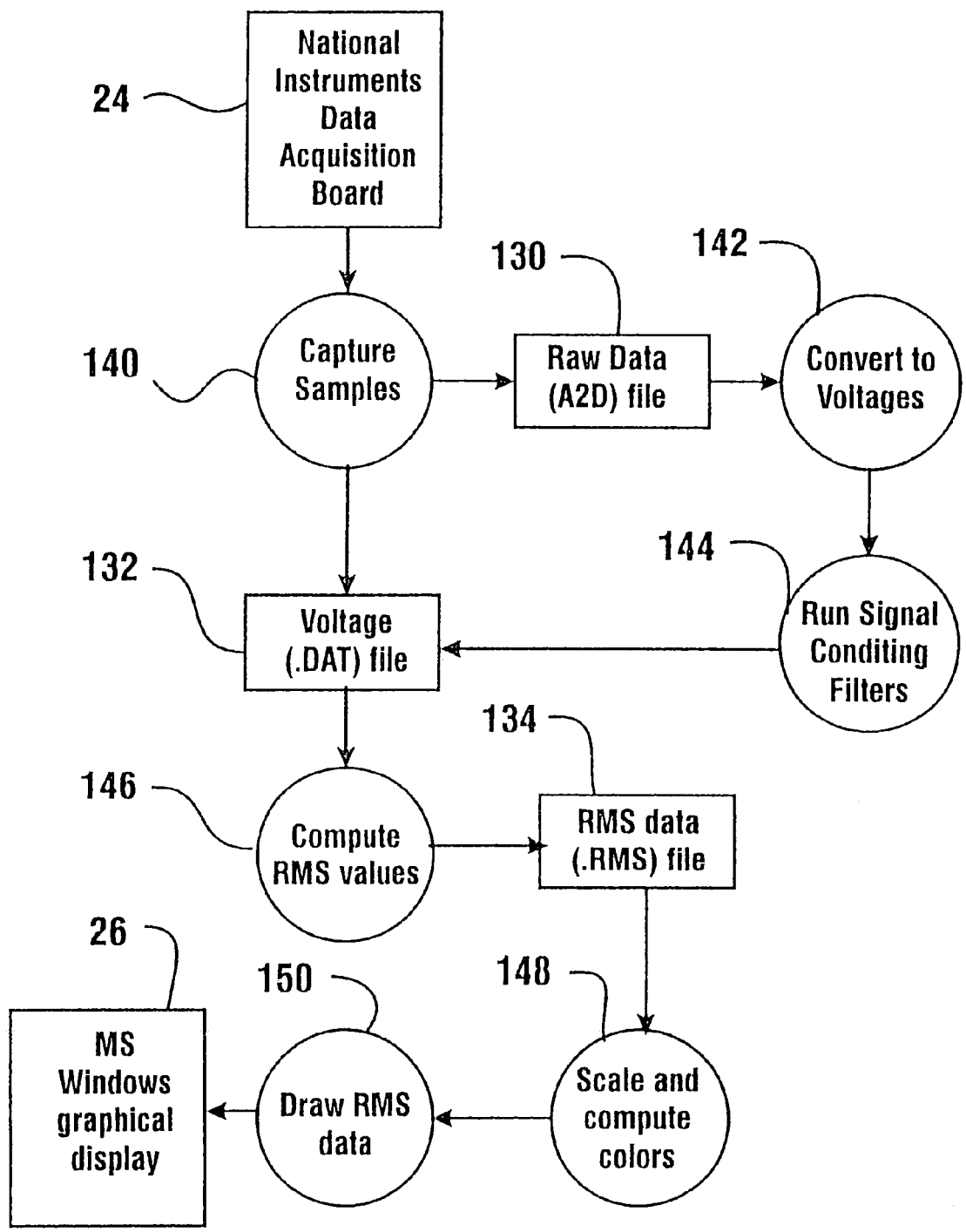
FIG. 27 is a logic diagram showing the data flow in the software of the system.

The software architecture of the signal processing system 102 is shown schematically in FIG. 27 as a diagram of the main data flow in the software. Essentially, this is a linear flow of computations, each of which takes a datum or file as input and generates a datum or file as output. Three types of data files are generated and stored and once created may be opened and displayed many times at later dates. The data files are described as well in FIG. 29 and comprise the Analog to Digital (A2D) file 130, Voltage (DAT) file 132 and Root Mean Square (RMS) file 134.

The format of header 135 for each of the files, 130, 132, 134 is depicted in FIG. 28 and in one embodiment contains information in an identical ASCII header format consisting of version information 152, patient information 154, which are the vital statistics on the patient being diagnosed, pad information 155 which provides specifics of sensor pad 10, calibration information 156, data acquisition settings 157 and display settings 158. The calibration information is derived after the sensor pad 10 location is determined on the back of the patient, being input by the operator to specify where certain parts of the patient's back are in relation to the electrodes on the pad, as previously described.

The A2D files 130 contain the actual analog to digital values at the output of analog to digital converter 24 which are collected during a test. Computer 25 scans all electrode channels rapidly enough to reconstruct the analog signal at all frequencies of interest. In one embodiment the minimum frequency of interest is about 30 Hz and the maximum about 150 Hz. The structure of the A2D files 130 is shown in FIG. 29 with each scan sample being stored in a two byte word in little endian format. The files 130 contain the analog to digital value and a header 135.

The voltage files 132 contain the voltage data from a test, after it has been converted from analog to digital values to voltages and signal conditioning filters have been applied. The voltage files 132 of this embodiment also contain the header 135 followed by the voltage values in the format shown in FIG. 29, each sample being stored as an IEEE double floating point value.

The RMS files 134 contain the RMS values of the differences between the voltage waveforms of adjacent electrodes 28. During display of an RMS file 134, the values can be mapped to colors and displayed as colored line segments or color bars 63 at display unit 26. Again, the RMS files 134 contain header 135 followed by the RMS information. The RMS voltage difference is calculated for each pair of adjacent electrodes 28. The row and column position of each of the two electrodes are also stored in the format described in FIG. 29. Also included is information of the minimum and maximum RMS value in each scan and the total number of adjacent electrode pairs.

Summarizing then, the flow of data as depicted in FIG. 27 occurs as computer 25 generates signals to capture samples 140 from data acquisition board 24 at the input to computer 25 to create raw data or A2D files 130. Computer 25 then acts to convert the signals to voltage at 142 and run signal conditioning filters 144 to create voltage files 132. Computer 25 is then programmed to compute the RMS values at 146 and create the RMS data file 134. Subsequently, computer 25 operates to scale and compute color values at 148, and then to draw the RMS data at 150 and eventually provide the color bar matrix 125 depicted in FIG. 3.

The general architecture for the software operated in computer 25 can be seen from the source file 160 structure depicted in FIG. 30. The document view and visual interface 161 contain main initialization, menu and toolbar commands, message handlers and document/view commands. Dialog popups 162 allow for entering patient information, calibration information and the like and for editing various parameters. Further files include data acquisition, filtering and calculation 163, reading and writing header information and data 164, utilities 165, and bitmaps, icons and resource files 166. These routines are fairly typical for handling the information flow in the ways specified previously and are well understood in the art, not requiring detailed description herein. Further scaling software components for correlating the stored anatomical data to the anatomy of the particular patient is also preferably provided.

Although certain embodiments of the present invention have been disclosed and specifically described herein, these embodiments are for purposes of illustration and are not meant to limit the present invention. Upon review of this specification, certain improvements, modifications, adaptations and variations upon the methods and apparatus disclosed which do not depart from the spirit of the present invention will immediately become apparent. Accordingly, reference should be had to the appended claims in order to ascertain the true scope of the present invention.

For example, the apparatus of the invention might be applied to areas of human anatomy other than the lower back musculature, most obviously to mid-back, upper back or neck areas. Still further, it would be feasible to apply the teachings of the invention to the extremities of the human patient or even to areas of the head. The present invention may also be applied to the analysis of signals from other types of sensors and the techniques described herein used in the diagnosis and treatment of other conditions. While the exemplary form of the invention is used in the diagnosis of conditions in human beings, the techniques and apparatus of the invention may also find applicability in diagnostic and treatment activities related to patients which comprise other living organisms.

In addition the teachings of the present invention may also be used for detecting the position and intensity of other electrical signals within areas of the anatomy of a living body. Various organs and systems are known to produce such electrical signals. The analysis of such signals and their correlation may provide useful information for diagnosis and treatment.

In addition systems of the present invention may be modified to provide therapeutic benefit as well as to serve a diagnostic function. For example electrode arrays may be used to provide electrical stimulus selectively in areas corresponding to the electrodes. Such electrical stimulus may be used to treat muscle or other disorders. By way of example an electrode array may be used to determine the identities of muscles which are the source of a spasmodic or pain condition in the manner previously discussed. Once such muscles have been identified appropriate electrical circuitry may be provided to deliver electrical stimulation selectively so as to treat the underlying muscular structures. Alternative approaches and techniques may be used based on the nature of the underlying conditions being detected and the appropriate method of treatment.

Thus the method and apparatus of the present invention achieve the above stated objectives, eliminates difficulties encountered in the use of prior devices and systems, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations herein are by way of examples and the invention is not limited to the details shown and described.

In the following claims any feature that is described as a means for performing a function shall be construed as encompassing any means capable of performing the recited function and shall not be limited to the particular means shown in the foregoing description or mere equivalents.

Having described the features, discoveries and principles of the invention, the manner in which it is constructed and operated and the advantages and useful results attained; the new and useful structures, devices, elements, arrangements, parts, combinations, systems, equipment, operations and relationships are set forth in the appended claims.

We claim:

1. A method comprising:
   a) applying an electrode array to a patient, wherein the array includes at least one flexible substrate with a plurality of electrically conductive electrodes thereon, wherein the at least one substrate includes a plurality of rows of perforations, wherein each row includes a plurality of the perforations, wherein in each row the perforations are spaced apart and substantially longitudinally aligned;
   b) monitoring electrical signals in the patient with the electrodes while the patient moves causing the electrode array to stretch in at least one dimension, wherein portions of the at least one substrate on opposed sides of at least one perforation spread apart;
   c) through operation of at least one computer, evaluating at least one medical condition with respect to the patient responsive to the electrical signals monitored in (b).

2. The method according to claim 1, wherein in (a) the electrodes are in electrical communication with the back of the patient, wherein (b) includes at least two of the electrodes moving with respect to each other responsive to back muscles of the patient at least one of stretching and contracting.

3. The method according to claim 2, wherein in (a) portions of the at least one substrate between spaced apart perforations in a first row are longitudinally offset from portions of the at least one substrate between spaced apart perforations in a second row adjacent to the first row.

4. The method according to claim 3, wherein in (a) the electrode array includes a plurality of electrically conductive traces in supporting connection with the substrate, wherein at least one trace extends to each electrode, wherein portions of the traces extend between the rows of perforations.

5. The method according to claim 2 wherein prior to (a) removing a cover sheet from a first side of the electrode array, wherein prior to (b) removing a release sheet from a second side of the electrode array.

6. The method according to claim 5 wherein in (a) the at least one substrate includes a plurality of further perforations therethrough, wherein the further perforations extend in generally surrounding relation of each of the electrodes and enable movement of each of the electrodes relative portions of the at least one substrate adjacent the further perforations, wherein prior to removing the release sheet, the release sheet is operative to limit movement of each of the electrodes relative the portions of the at least one substrate sheet adjacent the further perforations.

7. A method comprising:
   a) monitoring electrical signals from a plurality of electrically conductive electrodes in operative connection with a substrate while the electrodes remain in electrical communication with a patient and the patient moves causing the substrate to increase in length in at least one dimension, wherein the substrate includes a plurality of rows of perforations therethrough, wherein each row includes a plurality of the perforations, wherein in each row the perforations are spaced apart and substantially longitudinally aligned, wherein the substrate increases in length by spreading apart portions of the substrate on opposed sides of at least one perforation;
   b) through operation of at least one computer, evaluating at least one medical condition with respect to the patient responsive to at least a portion of the electrical signals monitored in (a).

8. The method according to claim 7, wherein in (a) the electrodes are in electrical communication with the back of the patient, wherein (a) includes at least two electrodes moving with respect to each other responsive to back muscles of the patient at least one of stretching and contracting.

9. A method of monitoring and evaluating electrical signals in a back of a patient using a plurality of electrically conductive electrodes mounted to the back of the patient, wherein the electrodes are mounted to a substrate, wherein the substrate includes a plurality of rows of perforations therethrough, wherein each row includes a plurality of the perforations, wherein in each row the perforations are spaced apart and substantially longitudinally aligned, wherein the method comprises:
   a) monitoring electrical signals associated with each of the plurality of electrically conductive electrodes with the patient in different positions that cause the portions of the substrate on opposed sides of at least one perforation to spread apart;
   b) through operation of at least one computer, evaluating at least one medical condition with respect to the patient responsive to at least a portion of the electrical signals monitored in (a).

* * * * *